United States Patent [19]

Matsui et al.

[11] Patent Number: 4,904,680

[45] Date of Patent: Feb. 27, 1990

[54] AMINO ACID DERIVATIVES HAVING ANTI-TUMOR ACTIVITY AND COMPOSITIONS CONTAINING THEM

[75] Inventors: Takashi Matsui; Mitsuo Nagano; Koichi Kitamura; Fusaaki Shimizu, all of Tokyo, Japan

[73] Assignee: Sankyo Company, Limited, Tokyo, Japan

[21] Appl. No.: 146,955

[22] Filed: Jan. 22, 1988

Related U.S. Application Data

[63] Continuation of Ser. No. 946,430, Dec. 23, 1986, abandoned, which is a continuation of Ser. No. 753,707, Jul. 10, 1985, abandoned.

[30] Foreign Application Priority Data

Jul. 13, 1984 [JP] Japan .................................. 59-145731

[51] Int. Cl.$^4$ .................. C07D 277/06; A61K 31/425
[52] U.S. Cl. .................... 514/365; 546/280; 548/200; 548/567; 548/568; 564/92; 564/155
[58] Field of Search ........................ 548/200; 546/280; 514/365

[56] References Cited

FOREIGN PATENT DOCUMENTS

| | | | |
|---|---|---|---|
| 1236519 | 3/1967 | Fed. Rep. of Germany | 514/365 |
| 1793613 | 9/1971 | Fed. Rep. of Germany | 514/365 |
| 2139641 | 2/1973 | Fed. Rep. of Germany | 514/365 |
| 363467 | 8/1981 | Fed. Rep. of Germany | 514/365 |
| 155267 | 7/1987 | Japan | 548/200 |

OTHER PUBLICATIONS

Baldwin et al, JACS 97, 5957 (1975).
Chemical Abstracts, vol. 98, May 23–Jun. 6, 1983.
Analytical Chemistry, vol. 56, May 1984.

*Primary Examiner*—Robert Gerstl
*Attorney, Agent, or Firm*—Frishauf, Holtz, Goodman & Woodward

[57] ABSTRACT

Amino acid amides of formula (I):

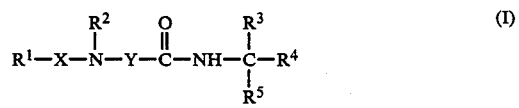

wherein $R^1$–$R^5$ and Y represent a variety of organic groups and atoms (including where $R^2$, Y and the adjacent nitrogen atom together represent a thiazolidine or pyrrolidine group) and X represents carbonyl or sulfonyl are mostly new compounds and have valuable anti-tumor and immuno-regulatory activities. They may be formulated in compositions for pharmaceutical use.

15 Claims, No Drawings

AMINO ACID DERIVATIVES HAVING ANTI-TUMOR ACTIVITY AND COMPOSITIONS CONTAINING THEM

This is a continuation of application Ser. No. 946,430, filed Dec. 23, 1986, which is a continuation of Ser. No. 753,707, filed July 10, 1985, both now abandoned.

BACKGROUND TO THE INVENTION

The present invention relates to a series of amino acid amides having anti-tumor activity, many of which are novel compounds, and provides a pharmaceutical composition for the treatment of tumors comprising these amino acid amides, as well as a method of treating tumors and immune deficiencies using them.

A number of compounds of the amino acid type have been proposed for use as anti-tumor agents. For example, Umezawa et al. [J. Antibiotics 29(8), 857–859 (1976)] disclose a compound called "bestatin", whose systematic name is [(2S, 3R)-3-amino-2-hydroxy-4-phenylbutanoyl]-L-leucine, and which is said to exhibit host-mediated anti-tumor activity; however, the structure of this compound differs markedly from that of the compounds of the present invention. U.S. patent application Ser. No. 597,817, filed Apr. 9, 1984, now U.S. Pat. No. 4,545,942 likewise discloses a series of amino acid derivatives having anti-tumor activities, but again the structure of these compounds is markedly different from that of the compounds of the present invention.

Compounds which may be represented by the formula:

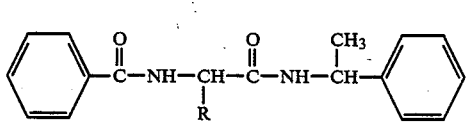

are disclosed in Chemical Abstracts, 98(23) 198680m (1983) (R represents an isopropyl group), Chemical Abstracts, 98(25) 215947Y (1983) (R represents a sec-butyl group) and Chemical Abstracts, 93(15) 150614n (1980) (R represents a benzyl group). Compounds of formula:

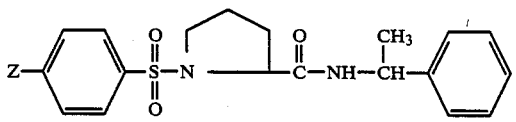

(in which Z represents a hydrogen atom, a nitro group, a chlorine atom or a methoxy group) are described in Analytical Chemistry, 56, 958–962 (1984). However, it is not disclosed that the compounds of the aforementioned Chemical Abstracts or of the Analytical Chemistry article have any therapeutic activity or value; all of these compounds are disclosed in the context of their use in analytical chemistry or in chemical synthesis.

We have now discovered that the compounds disclosed in the aforementioned Chemical Abstracts and the Analytical Chemistry article, as well as a group of closely related compounds, have excellent immunoregulatory and anti-tumor activities and are thus of potential value in the treatment of infections and of various malignant tumors, both in humans and in other animals.

BRIEF SUMMARY OF INVENTION

The compounds of the invention are those compounds of formula (I):

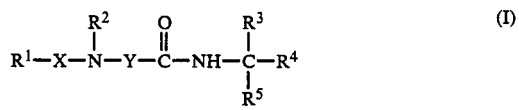

wherein:

$R^1$ represents a benzyl group, a phenyl group, a phenyl group having 1 or 2 substituents selected from the group consisting of $C_1$–$C_4$ alkyl, halogen, $C_1$–$C_4$ alkoxy, hydroxy, carboxy, nitro, trifluoromethyl, amino, $C_1$–$C_4$ alkylamino, dialkylamino wherein each alkyl part is $C_1$–$C_4$ alkyl, $C_1$–$C_4$ alkanoyl, cyano, carbamoyl, alkylcarbamoyl wherein the alkyl part is $C_1$–$C_4$ alkyl, dialkylcarbamoyl wherein each alkyl part is $C_1$–$C_4$ alkyl and $C_1$–$C_4$ alkylthio substituents, a naphthyl group, a thienyl group or a pyridyl group;

X represents a carbonyl (>C=O) or sulfonyl (>SO$_2$) group;

$R^2$ represents a hydrogen atom;

$R^3$ and $R^4$ are independently selected from the group consisting of hydrogen atoms and methyl groups;

Y represents a $C_1$–$C_5$ alkylene group or a $C_1$–$C_5$ alkylene group having one substituent selected from the group consisting of phenyl, benzyloxy, hydroxy, mercapto, $C_1$–$C_4$ alkylthio, benzylthio, carboxy, alkoxycarbonyl wherein the alkoxy part is $C_1$–$C_4$ alkoxy, cyano, carbamoyl, alkylcarbamoyl wherein the alkyl part is $C_1$–$C_4$ alkyl, amino, alkylamino wherein the alkyl part is $C_1$–$C_4$ alkyl and benzyloxycarbonylamino substituents; or $R^2$ and Y, together with the nitrogen atom to which they are attached, together represent a group of formula

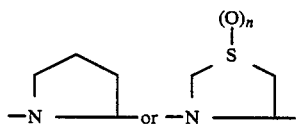

wherein n is 0, 1 or 2; and $R^5$ represents a $C_1$–$C_4$ alkyl group, a phenyl group, a phenyl group having 1 or 2 substituents selected from the group consisting of $C_1$–$C_4$ alkyl, halogen, $C_1$–$C_4$ alkoxy, hydroxy, carboxy, nitro, trifluoromethyl, amino, $C_1$–$C_4$ alkylamino, dialkylamino wherein each alkyl part is $C_1$–$C_4$ alkyl, $C_1$–$C_4$ acylamino, $C_1$–$C_4$ alkanoyl, cyano, carbamoyl, alkylcarbamoyl wherein the alkyl part is $C_1$–$C_4$ alkyl, dialkylcarbamoyl wherein each alkyl part is $C_1$–$C_4$ alkyl and $C_1$–$C_4$ alkylthio substituents.

All of the compounds defined above are novel and form a part of the present invention, except:

(a) those compounds in which X represents a sulfonyl group and $R^2$ and Y, together with the nitrogen atom to which they are attached, represent a group of formula

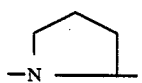

(certain of these compounds are disclosed in the aforementioned Analytical Chemistry article); and (b) those compounds where one or both of $R^3$ and $R^4$ represent hydrogen atoms and Y represents an unsubstituted alkylene group or a phenyl-substituted alkylene group (certain of these compounds are disclosed in the aforementioned Chemical Abstracts).

Accordingly, in one aspect, the present invention provides as novel compounds, compounds having the formula (I) as defined above, provided that:

(a) where X represents a sulfonyl group, $R^2$ and Y together with the nitrogen atom to which they are attached do not represent a group of formula

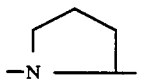

and (b) $R^3$ and $R^4$ both represent methyl groups when Y represents an unsubstituted alkylene group or phenyl-substituted alkylene group.

In another aspect, the present invention provides a pharmaceutical composition comprising an effective amount of an anti-tumor and immunoregulatory compound in admixture with a pharmaceutically acceptable carrier or diluent, wherein the anti-tumor and immunoregulatory compound is at least one compound of formula (I) as defined above.

In yet another aspect, the invention provides a method of treating a tumor or immune deficiency by administering to a mammal suffering from a tumor or immune deficiency an effective amount of an active compound, wherein the active compound is at least one compound of formula (I) as defined above.

DETAILED DESCRIPTION OF INVENTION

In the compounds of the invention, $R^1$ may represent a benzyl group, a phenyl group, a substituted phenyl group, a naphthyl group, a thienyl group or a pyridyl group. Where $R^1$ represents a naphthyl group, this may be a 1-naphthyl or 2-naphthyl group. Where $R^1$ represents a thienyl group, this may be a 2-thienyl or 3-thienyl group, preferably a 2-thienyl group. Where $R^1$ represents a pyridyl group, this may be a 2-pyridyl, 3-pyridyl or 4-pyridyl group, preferably a 3-pyridyl group.

Where $R^1$ represents a substituted phenyl group, it may have 1 or 2 substituents; where it has 1 substituent, this may be at the 2-, 3-, or 4-position; where it has 2 substituents, these may be at the 2,3-, 2,4-, 2,5-, 2,6-, 3,4- or 3,5-positions. The substituents are selected from the group consisting of $C_1$–$C_4$ alkyl groups, halogen atoms, $C_1$–$C_4$ alkoxy groups, hydroxy groups, carboxy groups, nitro groups, trifluoromethyl groups, amino groups, $C_1$–$C_4$ alkylamino groups, di($C_1$–$C_4$ alkyl)amino groups, $C_1$–$C_4$ acylamino groups, $C_1$–$C_4$ alkanoyl groups, cyano groups, carbamoyl groups, ($C_1$–$C_4$ alkyl)carbamoyl groups, di($C_1$–$C_4$ alkyl)carbamoyl groups and $C_1$–$C_4$ alkylthio groups.

Where the substituent is a $C_1$–$C_4$ alkyl group, this may be a straight or branched chain alkyl group and is more preferably a $C_1$–$C_3$ alkyl group. Examples of such alkyl groups include the methyl, ethyl, propyl, isopropyl, butyl, sec-butyl, isobutyl and t-butyl groups. Similarly, where the substituent is an alkylamino, dialkylamino, alkylcarbamoyl, dialkylcarbamoyl or alkylthio group, the alkyl group is or the alkyl groups are preferably selected from those exemplified above.

Where the substituent on the phenyl group represented by $R^1$ is a halogen atom, this may be a fluorine, chlorine, bromine or iodine atom.

Where the substituent is a $C_1$–$C_4$ alkoxy group, this may be a straight or branched chain alkoxy group and examples include the methoxy, ethoxy, propoxy, isopropoxy, butoxy, isobutoxy, sec-butoxy and t-butoxy groups, preferably the methoxy, ethoxy, propoxy, isopropoxy, butoxy and t-butoxy groups.

Where the substituent is a $C_1$–$C_4$ alkylamino group, the alkyl part may be any one of the alkyl groups exemplified above and examples of such alkylamino groups include the methylamino, ethylamino, propylamino, isopropylamino and butylamino groups.

Where the substituent is a dialkylamino group, each alkyl part is a $C_1$–$C_4$ alkyl group and the two alkyl parts may be the same or different, although they are preferably the same. Each alkyl part may be selected from any one of the alkyl groups exemplified above and preferred dialkylamino groups include the dimethylamino, diethylamino, dipropylamino and diisopropylamino groups.

Where the substituent on the phenyl group represented by $R^1$ is an acylamino group, the acyl part is a $C_1$–$C_4$ aliphatic carboxylic acyl group, which may be a straight or branched chain group and may have a saturated or unsaturated carbon chain, preferably a saturated carbon chain. Examples of such acylamino groups include the acetamido, propionamido and butyramido groups.

Where the substituent is a $C_1$–$C_4$ alkanoyl group, this may be a straight or branched chain group and examples include the formyl, acetyl, propionyl, butyryl and isobutyryl groups.

Where the substituent is an alkylcarbamoyl group, the alkyl part has from 1 to 4 carbon atoms and may be a straight or branched chain group, for example any of the alkyl groups exemplified above. Examples of such alkylcarbamoyl groups include the methylcarbamoyl, ethylcarbamoyl, propylcarbamoyl and butylcarbamoyl groups.

Where the substituent is a dialkylcarbamoyl group, each alkyl part is a $C_1$–$C_4$ alkyl group, which may be a straight or branched chain group, such as those alkyl groups exemplified above. The two alkyl groups may be the same or different, but are preferably the same. Examples of such dialkylcarbamoyl groups include the dimethylcarbamoyl, diethylcarbamoyl, dipropylcarbamoyl and diisopropylcarbamoyl groups.

Where the substituent is a $C_1$–$C_4$ alkylthio group, the alkyl part may be a straight or branched chain group and may be any one of the alkyl groups exemplified above. Preferred alkylthio groups are the methylthio, ethylthio, propylthio, isopropylthio and butylthio groups.

Y represents an alkylene group (i.e. a group derived by the removal of two hydrogen atoms from an alkane, the two hydrogen atoms being either from different carbon atoms or from the same carbon atom; the group where the 2 hydrogen atoms are removed from the same carbon atom is sometimes referred to as an "alkylidene" group) having from 1 to 5 carbon atoms. The alkylene group may be a straight or branched chain group and examples of such groups include the methylene, ethylene, ethylidene, trimethylene, propylene, propylidene, isopropylidene, tetramethylene, ethylethylene, methylpropylene, butylidene, pentamethylene, methyltetramethylene, ethyltrimethylene, propylethylene, pentylidene, methylbutylidene, methylpropylidene, and ethylpropylidene groups. These groups may be unsubstituted or may have a single substituent selected from the group consisting of phenyl, benzyloxy, hydroxy, mercapto, $C_1$–$C_4$ alkylthio, benzylthio, carboxy, ($C_1$–$C_4$ alkoxy)carbonyl, cyano, carbamoyl, alkylcarbamoyl, amino, alkylamino and benzyloxycarbonylamino substituents. In the case of the alkylthio, alkylcarbamoyl and alkylamino substituents, examples of these substituents are as given in relation to the corresponding substituents on the substituted phenyl group which may be represented by $R^1$. Where the substituent is an alkoxycarbonyl group, the alkoxy part is a $C_1$–$C_4$ alkoxy group which may be a straight or branched chain group and examples of such alkoxycarbonyl groups are the methoxycarbonyl, ethoxycarbonyl, propoxycarbonyl, isopropoxycarbonyl, butoxycarbonyl, isobutoxycarbonyl, sec-butoxycarbonyl and t-butoxycarbonyl groups.

As an alternative, $R^2$ and Y, together with the nitrogen atom to which they are attached, that is to say the group of formula

may represent a group of formula

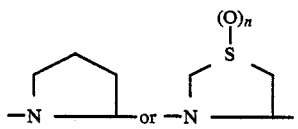

in which n is 0, 1 or 2, that is to say a pyrrolidine or thiazolidine ring system.

$R^5$ may represent a $C_1$–$C_4$ alkyl group, a phenyl group or a phenyl group having one or two substituents, as defined in relation to the substituted phenyl group represented by $R^1$. Where $R^5$ represents a $C_1$–$C_4$ alkyl group, examples are as given in relation to the alkyl groups which may be substituents on the substituted phenyl group represented by $R^1$. Where $R^5$ represents a substituted phenyl group, examples of the substituents are as given in relation to the substituents on the substituted phenyl group represented by $R^1$. Preferred substituted phenyl groups are phenyl groups having one or two substituents selected from the group consisting of $C_1$–$C_3$ alkyl groups, halogen atoms and hydroxy groups. Where there are 2 substituents, these may be the same or different.

One class of novel compounds of the present invention comprises those compounds of formula (I) in which:

$R^1$ represents a benzyl group, a phenyl group, a phenyl group having one or two substituents selected from the group consisting of $C_1$–$C_3$ alkyl, halogen, $C_1$–$C_4$ alkoxy, hydroxy, carboxy, nitro, amino, $C_1$–$C_4$ alkylamino, dialkylamino wherein each alkyl part is $C_1$–$C_4$, $C_1$–$C_4$ aliphatic carboxylic acylamino, cyano and $C_1$–$C_4$ alkylthio substituents, a naphthyl group, a thienyl group or a pyridyl group;

X represents a carbonyl or sulfonyl group;

$R^2$ represents a hydrogen atom;

Y represents a $C_1$–$C_5$ alkylene group or a $C_1$–$C_5$ alkylene group having a single substituent selected from the group consisting of phenyl, benzyloxy, hydroxy, mercapto, $C_1$–$C_4$ alkylthio, benzylthio, carboxy, alkoxycarbonyl wherein the alkoxy part is $C_1$–$C_4$ alkoxy, cyano, amino and $C_1$–$C_4$ alkylamino substituents;

$R^3$ and $R^4$ are independently selected from the group consisting of hydrogen atoms and methyl groups, provided that $R^3$ and $R^4$ are both methyl groups when Y represents an unsubstituted alkylene group or a phenyl-substituted alkylene group; and $R^5$ represents a $C_1$–$C_4$ alkyl group, a phenyl group or a phenyl group having 1 or 2 substituents selected from the group consisting of $C_1$–$C_3$ alkyl, halogen and hydroxy substituents.

Another class of novel compounds of the present invention comprises those compounds of formula (I) in which:

$R^1$ represents a benzyl group, a phenyl group, a phenyl group having one or two substituents selected from the group consisting of $C_1$–$C_3$ alkyl, halogen, $C_1$–$C_4$ alkoxy, hydroxy, carboxy, nitro, amino, $C_1$–$C_4$ alkylamino, dialkylamino wherein each alkyl part is $C_1$–$C_4$, $C_1$–$C_4$ aliphatic carboxylic acylamino, cyano and $C_1$–$C_4$ alkylthio substituents, a naphthyl group, a thienyl group or a pyridyl group;

X represents a carbonyl or sulfonyl group;

$R^2$, Y and the nitrogen atom to which they are both attached together represent a group of formula

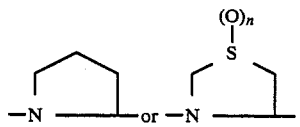

in which n is 0, 1 or 2, provided that X represents a carbonyl group when $R^2$, Y and said nitrogen atom together represent said group of formula

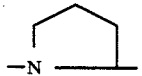

$R^3$ and $R^4$ are independently selected from the group consisting of hydrogen atoms and methyl groups; and $R^5$ represents a $C_1$–$C_4$ alkyl group, a phenyl group or a phenyl group having 1 or 2 substituents selected from the group consisting of $C_1$–$C_3$ alkyl, halogen and hydroxy substituents.

A preferred class of compounds of the present invention comprises those compounds in which:

$R^1$ represents a benzyl group, a phenyl group or a phenyl group having 1 or 2 halogen substituents;

Y represents a $C_1$–$C_5$ alkylene group or a $C_1$–$C_5$ alkylene group having one substituent selected from the group consisting of phenyl, benzyloxy, hydroxy, mercapto, carboxy and $C_2$–$C_5$ alkoxycarbonyl substituents; and $R^5$ represents $C_1$–$C_4$ alkyl group or a phenyl group.

Another preferred class of novel compounds of the present invention comprises those compounds in which:

$R^1$ represents a phenyl group;

X represents a carbonyl group;

$R^2$ and Y, together with the nitrogen atom to which they are attached, represent a group of formula

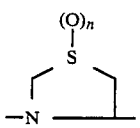

in which n is 0, 1 or 2;

$R^3$ and $R^4$ are independently selected from the group consisting of hydrogen atoms and methyl groups; and $R^5$ represents the phenyl group.

It will be appreciated that, depending upon the nature of various of the substituents, the compounds of the present invention may contain one or more asymmetric carbon atoms and accordingly various optical isomers and diastereoisomers may be possible. The present invention envisages both the individual isolated isomers and mixtures (which may be racemates) of these isomers.

Specific examples of compounds of the present invention are given in the following Tables. In these Tables, the following abbreviations are used:

Ac=acetyl;
Bzc=benzyloxycarbonyl;
Bz=benzyl;
Et=ethyl;
Me=methyl;
Nt=naphthyl (the position of attachment of the naphthyl group to the remainder of the molecule is identified by appending a suitable number to the abbreviation "Nt");
Ph=phenyl (substituted phenyl groups are designated by appending the substituent to the abbreviation "Ph" and identifying the position of attachment of the substituent to the phenyl group);
Pi=propionyl;
Py=pyridyl (the position of attachment of the pyridyl group to the remainder of the molecule is identified by appending the appropriate number to the abbreviation "Py");
tBu=t-butyl;
Th=thienyl (the position of attachment of the thienyl group to the remainder of the molecule is identified by appending a suitable number to the abbreviation "Th").

As noted above, various of the compounds can exist in the form of optical isomers and diastereoisomers. In some cases, the configuration of one or more of the asymmetric carbon atoms is specified by "$\underline{R}$", "$\underline{S}$" or "$\underline{RS}$"; where no such configuration is specifically identified, the configuration of the asymmetric carbon atom is "$\underline{RS}$".

In the following Tables, for certain of the Compounds identified therein, a configuration is indicated. It should be noted that configurations are indicated in these Tables solely for the convenience of identifying Compounds hereafter by the Compound Nos. assigned to them in these Tables and that the invention embraces Compounds of any configuration (regardless of the configuration specified in these Tables) as well as mixtures of isomers of these Compounds.

Where a configuration is specified under the column headed "Y", this refers to the configuration of the carbon atom of the group Y by which the group Y is attached to the remainder of the molecule.

Where the configuration is specified under the column headed "$R^5$", this refers to the configuration of the carbon atom to which the group represented by $R^5$ is attached.

Where a configuration is specified under the column headed "$\underline{n}$", this refers to the configuration of the 1-oxothiazolidine sulfur atom.

Compounds of formula (I-1) are as defined in the following Table 1:

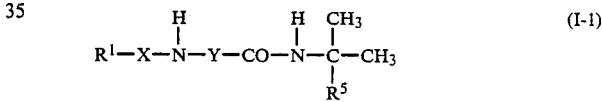

TABLE 1

| Cpd No | $R^1$ | X | Y | $R^5$ |
|---|---|---|---|---|
| 1 | Ph | CO | —CH₂— | Ph |
| 2 | Ph | CO | >CH—Me($\underline{S}$) | Ph |
| 3 | Ph | CO | —(CH₂)₂— | Ph |
| 4 | Ph | CO | >CH—CH₂CH(Me)₂ | Ph |
| 5 | Ph | CO | >CH—Me | Ph |
| 6 | 2,6-diCl—Ph | CO | —CH₂— | Ph |
| 7 | 2,6-diF—Ph | CO | —CH₂— | Ph |
| 8 | Ph | CO | —CH₂— | Et |
| 9 | 4-Cl—Ph | SO₂ | —CH₂— | Ph |
| 10 | Bz | SO₂ | —CH₂— | Ph |
| 11 | 2-Th | CO | —CH₂— | Ph |
| 12 | Ph | CO | >CHCH(Me)Et($\underline{S}$) | Ph |
| 13 | Ph | CO | >CHCH₂OBz($\underline{S}$) | Ph |
| 14 | Ph | CO | >CHCH₂OH($\underline{S}$) | Ph |
| 15 | Ph | CO | >CH(CH₂)₂SMe($\underline{S}$) | Ph |

TABLE 1-continued

| Cpd No | R¹ | X | Y | R⁵ |
|---|---|---|---|---|
| 16 | Ph | CO | >C(Me)₂ | Ph |
| 17 | Ph | CO | >CH—Me(R) | Ph |
| 18 | Ph | CO | >CHCH₂SH(R) | Ph |
| 19 | Ph | CO | >CH(CH₂)₄NHBzc(S) | Ph |
| 20 | Ph | CO | >CH(CH₂)₄NH₂(S) | Ph |
| 21 | 4-Cl—Ph | CO | >C(Me)CH₂CH₂CN | Ph |
| 22 | 4-Cl—Ph | CO | >C(Me)CH₂CH₂CONH₂ | Ph |
| 23 | 4-Cl—Ph | CO | >C(Me)CH₂COOMe | Ph |
| 24 | 4-Cl—Ph | CO | >C(Me)CH₂COOH | Ph |
| 25 | 4-Cl—Ph | CO | —C(Me)(COOH)CH₂— | Ph |
| 26 | Ph | CO | >CHCH₂Ph | Ph |
| 27 | 3-Py | CO | —CH₂— | Ph |
| 28 | 3-Th | CO | —CH₂— | Ph |
| 29 | Ph | CO | —CH₂— | 2-Cl—Ph |
| 30 | Ph | CO | —CH₂— | 3-Cl—Ph |
| 31 | Ph | CO | —CH₂— | 4-Cl—Ph |
| 32 | Ph | CO | —CH₂— | 2-F—Ph |
| 33 | Ph | CO | —CH₂— | 4-F—Ph |
| 34 | Ph | CO | —CH₂— | 4-Me—Ph |
| 35 | Ph | CO | —CH₂CH₂— | 4-Cl—Ph |
| 36 | Ph | CO | >CH—Me | 4-Cl—Ph |
| 37 | Ph | CO | >CH—Me | 4-F—Ph |
| 38 | 4-Cl—Ph | CO | >C(Me)CH₂CH₂CN(R) | Ph |
| 39 | 4-Cl—Ph | CO | >C(Me)CH₂CH₂CONH₂ | Ph |
| 40 | 4-Cl—Ph | CO | >C(Me)CH₂COOMe | Ph |
| 41 | 4-Cl—Ph | CO | >C(Me)CH₂COOH | Ph |
| 42 | Bz | SO₂ | >C(Me)CH₂CH₂CN | Ph |
| 43 | 2,6-diF—Ph | CO | >C(Me)CH₂CH₂CN | Ph |
| 44 | Ph | CO | >CHCH₂OH | Ph |
| 45 | Bz | SO₂ | >CHCH₂OH(R) | Ph |
| 46 | Bz | SO₂ | >CHCH₂OH(S) | Ph |
| 47 | 2,6-diF—Ph | CO | >CHCH₂OH | Ph |
| 48 | Ph | CO | >CHCH(OH)Me | Ph |
| 49 | 2-Nt | CO | —CH₂— | Ph |

TABLE 1-continued

| Cpd No | R¹ | X | Y | R⁵ |
|---|---|---|---|---|
| 50 | 3-NH₂—Ph | CO | >CH—Me | Ph |
| 51 | 4-MeNHCO—Ph | CO | —CH₂— | Ph |
| 52 | 4-NH₂—Ph | CO | >CHCH₂OH | 4-OH—Ph |
| 53 | 3-NH₂CO—Ph | SO₂ | >CH(CH₂)₃Me | Ph |

Compounds having the formula (I-2) are as defined in the following Table 2:

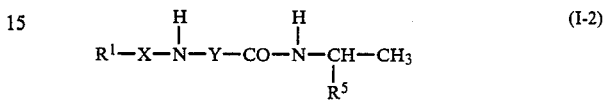

(I-2)

TABLE 2

| Cpd No | R¹ | X | Y | R⁵ |
|---|---|---|---|---|
| 54 | Ph | CO | —CH₂— | Ph |
| 55 | Ph | CO | —(CH₂)₃— | Ph |
| 56 | Ph | CO | >CHCH₂Me | Ph |
| 57 | Ph | CO | >C(Me)₂ | Ph |
| 58 | Ph | CO | —(CH₂)₅— | Ph |
| 59 | Ph | CO | >CH(CH₂)₃Me | Ph |
| 60 | Ph | CO | >CH—Me(S) | Ph |
| 61 | Ph | CO | >CH—Me(R) | Ph |
| 62 | Ph | CO | >CH—Me | Ph |
| 63 | Ph | CO | >CHCH₂CH(Me)₂ | Ph |
| 64 | Ph | CO | >CHCH₂CH₂SMe | Ph |
| 65 | Ph | CO | >CHPh | Ph |
| 66 | Ph | CO | —CH₂CH₂— | Ph |
| 67 | 4-Cl—Ph | CO | —CH₂— | Ph |
| 68 | 3,4-diCl—Ph | CO | —CH₂— | Ph |
| 69 | 4-Me—Ph | CO | —CH₂— | Ph |
| 70 | 4-MeO—Ph | CO | —CH₂— | Ph |
| 71 | 4-NO₂—Ph | CO | —CH₂— | Ph |
| 72 | 4-tBu—Ph | CO | —CH₂— | Ph |
| 73 | 3-CF₃—Ph | CO | —CH₂— | Ph |
| 74 | 2,6-diCl—Ph | CO | —CH₂— | Ph |
| 75 | 2,6-diF—Ph | CO | —CH₂— | Ph |
| 76 | Ph | CO | —CH₂— | Ph(S) |
| 77 | Ph | CO | —CH₂— | Ph(R) |
| 78 | Ph | CO | >CH—Me(S) | Ph(R) |
| 79 | Ph | CO | >CH—Me(S) | Ph(S) |
| 80 | 4-Cl—Ph | CO | >CH—Me | Ph |
| 81 | 4-Cl—Ph | CO | >CHCH(Me)Et | Ph |
| 82 | 4-Cl—Ph | CO | >C(Me)CH₂CH₂CN(R) | Ph(R) |

TABLE 2-continued

| Cpd No | R¹ | X | Y | R⁵ |
|---|---|---|---|---|
| 83 | 4-Cl—Ph | CO | >C(Me)CH₂CH₂CN(S) | Ph(R) |
| 84 | 4-Cl—Ph | CO | >C(Me)CH₂CH₂CN(S) | Ph(S) |
| 85 | 4-Cl—Ph | CO | >C(Me)CH₂CH₂CN(R) | Ph(S) |
| 86 | Bz | SO₂ | >C(Me)CH₂CH₂CN(R) | Ph |
| 87 | Bz | SO₂ | >C(Me)CH₂CH₂CN(S) | Ph |
| 88 | 2,6-diF—Ph | CO | >C(Me)CH₂CH₂CN(R) | Ph |
| 89 | 2,6-diF—Ph | CO | >C(Me)CH₂CH₂CN(S) | Ph |
| 90 | Ph | CO | >CHCH₂OH(R) | Ph |
| 91 | Ph | CO | >CHCH₂OH(S) | Ph |
| 92 | Ph | CO | >CHCH(OH)Me(R) | Ph |
| 93 | Ph | CO | >CHCH(OH)Me(S) | Ph |
| 94 | 3-Ac—Ph | CO | —CH₂— | Ph |
| 95 | Bz | SO₂ | >CHCH₂OPh | 4-OH—Ph |
| 96 | 2,6-diCl—Ph | CO | —CH₂— | 4-OH—Ph |

Compounds having the formula (I-3) are defined in the following Table 3:

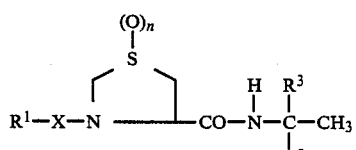

(I-3)

TABLE 3

| Cpd No | R¹ | X | n | R³ | R⁵ | 4-Conf |
|---|---|---|---|---|---|---|
| 97 | Ph | CO | 0 | Me | Ph | S |
| 98 | Ph | CO | 0 | H | Ph | S |
| 99 | Bz | SO₂ | 0 | H | Ph(S) | S |
| 100 | Bz | SO₂ | 0 | H | Ph(R) | S |
| 101 | 2,6-diF—Ph | CO | 0 | H | Ph(S) | S |
| 102 | 2,6-diF—Ph | CO | 0 | H | Ph(R) | S |
| 103 | Bz | SO₂ | 0 | H | Ph(S) | R |
| 104 | Bz | SO₂ | 0 | H | Ph(R) | R |
| 105 | 2,6-diF—Ph | CO | 0 | H | Ph(S) | R |
| 106 | 2,6-diF—Ph | CO | 0 | H | Ph(R) | R |
| 107 | 4-AcNH—Ph | CO | 0 | H | Ph | — |
| 108 | 4-CN—Ph | CO | 1 | H | Ph | — |
| 109 | 4-NH₂CO—Ph | CO | 0 | H | Ph | — |
| 110 | 4-MeS—Ph | CO | 0 | H | Ph | — |
| 111 | 4-OH—Ph | CO | 2 | H | 3-OH—Ph | — |
| 112 | 3-OH-5-Pi—Ph | CO | 1 | H | 4-OH—Ph | — |
| 113 | 3-MeNH—Ph | CO | 0 | H | 3-OH—Ph | — |
| 114 | 3-CN—Ph | CO | 0 | H | 4-OH—Ph | — |
| 115 | Ph | CO | 0 | H | Ph(R) | R |
| 116 | Ph | CO | 0 | H | Ph(S) | R |
| 117 | Ph | CO | 0 | H | Ph(S) | S |
| 118 | Ph | CO | 0 | H | Ph(R) | S |
| 119 | Ph | CO | 0 | H | Ph | R |

TABLE 3-continued

| Cpd No | R¹ | X | n | R³ | R⁵ | 4-Conf |
|---|---|---|---|---|---|---|
| 120 | Ph | CO | 0 | H | 4-OH—Ph(R) | R |
| 121 | Ph | CO | 1(S) | H | 4-OH—Ph(R) | R |
| 122 | 4-OH—Ph | CO | 0 | H | Ph(R) | R |
| 123 | 4-Me—Ph | CO | 0 | H | Ph(R) | R |
| 124 | 2-Th | CO | 0 | H | Ph(R) | R |
| 125 | 3-Py | CO | 0 | H | Ph(R) | R |
| 126 | Ph | CO | 0 | Me | 4-Cl—Ph | R |
| 127 | Ph | CO | 1(R) | H | Ph(R) | R |
| 128 | Ph | CO | 1(S) | H | Ph(R) | R |
| 129 | Ph | CO | 2 | H | Ph(R) | R |
| 130 | Ph | CO | 1(R) | H | 4-OH—Ph(R) | R |
| 131 | Ph | CO | 2 | H | 4-OH—Ph(R) | R |
| 132 | 4-F—Ph | CO | 0 | H | Ph(R) | R |

In the above and following Tables, the column headed "4-Conf." identifies the configuration of the carbon atom at the 4-position of the thiazolidine ring.

Compounds having the formula (I-4) are as defined in the following Table 4:

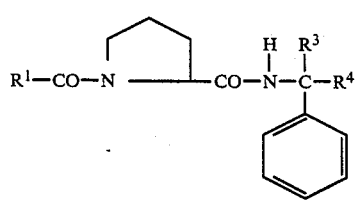

(I-4)

TABLE 4

| Cpd No | R¹ | R³ | R⁴ | 4-Conf. |
|---|---|---|---|---|
| 133 | Ph | H | Me | S |
| 134 | 4-MeNH—Ph | Me | Me | — |
| 135 | 3-MeS—4-OH—Ph | H | H | — |
| 136 | Ph | Me | Me | S |

Other examples of the specific compounds of the invention are:
137. 3-(4-fluoro-3-hydroxybenzoyl)-4-benzylcarbamoyl-1-oxothiazolidine.
138. (4R)-3-benzoyl-4-benzylcarbamoylthiazolidine.
139. (4R)-3-benzoyl-4-(2,4-dichlorobenzylcarbamoyl)-thiazolidine.

Of the compounds listed above, preferred compounds are as follows:
(2S)-N-(α,α-Dimethylbenzyl)-2-benzoylamino-3-benzyloxypropionamide (Compound No. 13)
(2S)-N-(α,α-Dimethylbenzyl)-3-hydroxy-2-benzoylaminopropionamide (Compound No. 14)
(2R)-N-(α,α-Dimethylbenzyl)-2-benzoylamino-3-mercaptopropionamide (Compound No. 18)
N-(α,α-Dimethylbenzyl)-2-(2,6-dichlorobenzoylamino)acetamide (Compound No. 6)
3-Benzoyl-4(S)-(α-methylbenzylcarbamoyl)thiazolidine (Compound No. 98)
N-(α-Methylbenzyl)-2-(2,6-difluorobenzoylamino)acetamide (Compound No. 75)
(4R)-3-Benzoyl-4-[(R)-α-methylbenzylcarbamoyl]-thiazolidine (Compound No. 115)
(4R)-3-Benzoyl-4-[(S)-α-methylbenzylcarbamoyl]-thiazolidine (Compound No. 116)
(4S)-3-Benzoyl-4-[(S)-α-methylbenzylcarbamoyl]-thiazolidine (Compound No. 117)
(4S)-3-Benzoyl-4-[(R)-α-methylbenzylcarbamoyl]-thiazolidine (Compound No. 118)
(4R)-3-Benzoyl-4-[(RS)-α-methylbenzylcarbamoyl]-thiazolidine (Compound No. 119)
(1R,4R)-3-Benzoyl-4-[(R)-α-methylbenzylcarbamoyl]-1-oxothiazolidine (Compound No. 127)
(1S,4R)-3-Benzoyl-4-[(R)-α-methylbenzylcarbamoyl]-1-oxothiazolidine (Compound No. 128)
(4R)-3-Benzoyl-4-[(R)-α-methylbenzylcarbamoyl]-1,1-dioxothiazolidine (Compound No. 129) and
(4R)-3-Benzoyl-4-benzylcarbamoylthiazolidine (Compound No. 138).

The compounds of the invention contain at least one carbonyl group and at least two amino or amido nitrogen atoms in their main chain. They may, accordingly, be prepared by well-known condensation reactions in two or more stages to link together the various component parts of the main chain of the compounds of formula (I).

For example, the compounds of the invention may be prepared by reacting a compound of formula (II):

$$R^1XA \qquad (II)$$

[in which R¹ and X are defined above and A represents either (a) a hydroxy group or (b) a group of formula —N(R²)YCOH] or a reactive derivative thereof with a compound of formula (III):

$$B-NH-CR^3R^4R^5 \qquad (III)$$

[in which R³, R⁴ and R⁵ are as defined above and B represents either (a) a group of formula HN(R²)YCO— or (b) a hydrogen atom] or a reactive derivative thereof, if necessary in the presence of a condensing agent.

Presented as a 2-stage process, the process preferably comprises reacting together a compound of formula (IV):

$$R^1XOH \qquad (IV)$$

(in which R¹ and X are as defined above) or a reactive derivative thereof, a compound of formula (V):

$$R^2HNYCOOH \qquad (V)$$

(in which R² and Y are as defined above) or a reactive derivative thereof and a compound of formula (VI):

$$H_2NCR^3R^4R^5 \qquad (VI)$$

(in which R³, R⁴ and R⁵ are as defined above) or a reactive derivative thereof, if necessary in the presence of a condensing agent, and either in the order [(IV)+(V)]+(VI) or in the order [(V)+(VI)]+(IV).

Where a reactive derivative of the compound of formula (IV) is employed, this is preferably the carboxylic acid halide (where X represents a carbonyl group) or the sulfonyl halide (where X represents a sulfonyl group) or an acid anhydride, which can be a mixed acid anhydride. Preferred halides are the chlorides and bromides.

Similarly, suitable reactive derivatives of the compounds of formulae (II), (III), (V) and (VI) are well known in the art. The reactive derivative of the compound of formula (II), (III), (IV), (V) and (VI) may also include a compound of this formula in which any reactive group other than the group which it is desired should take part in the reaction has been protected.

In one embodiment of the process of the invention, a first stage comprises reacting the compound of formula (IV), or reactive derivative thereof, with a compound of formula (V).

Where a carboxylic acid halide or sulfonyl halide of the compound of formula (IV) is employed, the reaction is preferably effected in the presence of a base and of a suitable solvent. A wide range of bases may be employed for this reaction, for example: alkaline compounds of metals, particularly alkali metals or alkaline earth metals, such as alkali metal hydroxides (such as sodium hydroxide or potassium hydroxide) or alkali metal carbonates (such as sodium carbonate or potassium carbonate); or organic amines, such as triethylamine, pyridine or picoline. The nature of the solvent employed is not critical, provided that it does not adversely affect the reaction. Suitable solvents include: water; alcohols, such as methanol; glycol monoethers, such as ethylene glycol monomethyl ether; ethers, such as dioxane; halogenated hydrocarbons, particularly halogenated aliphatic hydrocarbons, such as methylene chloride or chloroform; aromatic hydrocarbons, such as benzene or toluene; and amides, such as dimethylformamide or dimethylacetamide. The reaction will take place over a wide range of temperatures, for example a temperature from 0° C. to 100° C. The time required for the reaction will vary, depending upon many factors, including the nature of the reagents and the reaction temperature, but a period from 30 minutes to 2 hours will normally suffice.

The product of the reaction of the compounds of formulae (IV) and (V) is a compound of formula (VII):

$$R^1X—R^2N—YCOOH \quad (VII)$$

(in which $R^1$, $R^2$, X and Y are as defined above). This compound may, if desired, be purified by conventional means or it may be employed without any intermediate purification in the next stage of the reaction.

Alternatively, where the free acid of formula (IV) is reacted with the amino acid of formula (V), the reaction is preferably effected in the presence of a condensing agent. Condensing agents which may be employed in this reaction are well-known to those skilled in the art for the reaction of acids and amines and examples include dicyclohexylcarbodiimide, carbonyldiimidazole, diethyl cyanophosphate, diphenylphosphoryl azide, 2,2'-dipyridyl disulfide and methylpyridinium halides. Otherwise, the reaction conditions, including temperature and reaction time, as well as the preferred reaction solvents, are as employed in the reaction of a reactive derivative of the compound of formula (IV) with the amino acid (V).

In the second stage of this reaction, the resulting compound of formula (VII) is reacted with the amine of formula (VI). This reaction is preferably effected in the presence of a condensing agent, examples of which are given above in relation to the reaction of the free acid of formula (IV) with the amino acid (V). Alternatively, the reaction may be effected by first treating the intermediate of formula (VII) with such a condensing agent to form an azalactone and then reacting this azalactone with the compound of formula (VI). A further alternative is to prepare a mixed acid anhydride by reacting the intermediate of formula (VII) with an alkoxycarbonyl chloride (such as ethoxycarbonyl chloride, isobutoxycarbonyl chloride or benzyloxycarbonyl chloride) in the presence of a base (such as triethylamine, pyridine or diazabicyclo[5.4.0]undecene-7). The mixed acid anhydride is then reacted with the amine of formula (VI). The reaction is preferably effected in the presence of a solvent, the nature of which is not critical, provided that it has no adverse effect upon the reaction. Suitable solvents are as exemplified above in relation to the reaction of the compounds of formulae (IV) and (V). The reaction will take place over a very wide range of temperatures, for example from $-20°$ C. to $+150°$ C. and the time required for the reaction will normally be within the range from 30 minutes to 2 hours.

The resulting compound of formula (I) thus obtained can be isolated by conventional techniques, the precise technique employed depending, as is well-known in the art, upon the nature of the reagents and of the reaction solvent. The compound may then, if desired, be purified by various conventional means. A suitable isolation and purification sequence would comprise: washing, extraction, condensation of the extract, recrystallization and column chromatography.

An alternative reaction sequence comprises reacting the compounds of formulae (V) and (VI) in a first stage, to prepare a compound of formula (VIII):

$$R^2—NH—YCO—NH—CR^3R^4R^5 \quad (VIII)$$

(in which $R^2$, $R^3$, $R^4$, $R^5$ and Y are as defined above) and then reacting this compound of formula (VIII) with the compound of formula (IV).

In the first stage of this process, we prefer that the amino group of the compound of formula (V) should be protected prior to reaction of that compound with the compound of formula (VI). Protecting groups which may be employed for this purpose are well-known to those skilled in the art; examples include alkoxycarbonyl and aryl-substituted alkoxycarbonyl groups, such as the isobutoxycarbonyl and benzyloxycarbonyl groups. The condensation reaction of the compound of formula (V), or the protected equivalent of the compound of formula (V), with the compound of formula (VI) can be effected under the same conditions as are described in relation to the condensation of the intermediate of formula (VII) with the compound of formula (VI) above.

The resulting compound of formula (VIII), or its protected equivalent, can then be purified by conventional means, if necessary, or it may be employed without intermediate purification. Where a protected equivalent of the compound of formula (VIII) is prepared, the protecting group is first removed by conventional means and then the resulting compound of formula (VIII) is reacted with the compound of formula (IV). This reaction may be carried out under the same conditions as are described above for the reaction of the compounds of formulae (IV) and (V).

Following this reaction, the compound thus obtained may be isolated and purified, e.g. as described above.

Where the compound of formula (I) prepared by any of the processes described above is prepared as a mixture of optical isomers, these isomers may be separated by conventional resolution techniques. Alternatively, by employing as starting materials individual optical isomers of the compounds of formula (IV), (V) and (VI), stereo-specific synthesis of a desired individual isomer of the compound of formula (I) may be achieved.

The compounds of general formula (I), most of which are novel, have such excellent immunomodulating or immunoregulatory and anti-tumor activities that they are useful as therapeutic and preventative agents against various kinds of infections and malignant tumors. Their pharmacological effects are illustrated as follows.

1. Restoration of Immune Function in Tumor-bearing Mice

Ehrlich carcinoma ascites cells were transplanted into female ICR/JCL strain mice. Mice into which the tumor cells had not been transplanted were used as controls. A delayed-type hypersensitive reaction caused by BCG (bacillus Calmette-Guerin), as an antigen, was investigated in the footpat swelling reactions of mice. The mice were employed in groups of 10 for each experiment.

Nine days before immunization, $2\times10^6$ Ehrlich carcinoma ascites cells were transplanted subcutaneously to the axilla of each mouse. 500 μg of BCG were subcutaneously injected into the back of each mouse in order to immunize it. Fourteen days after this immunization, 500 μg of BCG were injected intradermally into the hind foot pad as a challenging injection to elucidate the foot pad swelling reactions. After 24 hours, the difference between the swelling of the foot pad which had been challenged and that of a foot pad of the animal which had not challenged with BCG was determined. Normal animals used as the control were immunized and challenged with BCG in a similar manner. The test compound was suspended or dissolved in physiological saline solution containing 0.25% carboxymethylcellulose, and administered orally or intraperitoneally in an amount, respectively, of 1 mg or 10 mg per kg, twice, once 4 and once 2 days before immunization.

Bestatin, levamiscole and forphenicinol, which are used clinically as antitumor immunotherapeutic agents, were administered in a similar manner for purposes of comparison.

The restoration of immune function in the tumor-bearing animals was evaluated as the restorative rate calculated according to the following equation.

$$\text{Recovery rate} = 100 - \left[\frac{Fn - Ft}{Fn - Fw} \times 100\right]$$

Where
Fn=Footpat swelling of the normal control animal
Ft=Footpat swelling of the tumor-bearing animal given the test compound
Fw=Footpat swelling of the tumor-bearing animal without treatment From the results of statistical studies, it is clear that, where the restorative rate is 80% or more, there is no significant difference between the footpad reaction of the tumor-bearing animal given the test compound and that of a normal control animal. Accordingly, a 80% or greater restorative rate observed after administration of any dose of the test compound is considered to be a significant immune-restorative effect and is evaluated as "+". A restorative rate of from 70 to 80% is considered to indicate a tendency to restore the activity of the immune system and is evaluated as "±". The results are shown in Table 5.

TABLE 5

| Compound No. | Immunerestorative effect |
|---|---|
| 1 | + |
| 2 | + |
| 6 | + |
| 13 | + |
| 14 | + |
| 18 | + |
| 23 | + |
| 60 | + |
| 63 | + |
| 65 | + |
| 98 | + |
| 115 | + |
| 117 | + |
| 118 | + |
| 119 | + |
| 127 | + |
| 128 | + |
| 129 | + |
| 130 | + |
| 133 | + |
| Bestatin | − |
| Levamisole | ± |
| Forphenicinol | − |

In this and subsequent Tables, the compounds of the invention are identified by the numbers heretofor assigned to them in Tables 1–4.

The results given in Table 5 indicate that the compounds of the invention have the ability to restore the immune response from the low level of tumor-bearing mice to essentially the same level as in normal mice.

2. Anti-tumor activity against transplanted tumors

In this experiment, the MH-134 mouse hepatoma strain of tumor cell was selected because it is a syngenic tumor which is extremely malignant and frequently metastasizes from the transplanted region to normal tissues. The anti-tumor effect of the compounds of the invention was studied in combination with a known anti-tumor chemotherapeutic agent, to evaluate the ability of the compound to potentiate the activity of such a known chemotherapeutic anti-tumor agent.

Into the axilla of female mice of the $C_3H/HeN-Crj$ strain were transplanted subcutaneously $2 \times 10^6$ MH-134 tumor cells. Seven days after transplantation, when the transplanted tumor had grown to about 10 mm diameter, 2 mg/kg of carboquone, a known anti-tumor chemotherapeutic agent, was administered intravenously. At the same time, 0.1 mg/kg, 1.0 mg/kg or 10 mg/kg of the test compound was administered orally for 5 consecutive days beginning on the seventh day after transplantation.

The test compound was dissolved in a small amount of Tween 80 (trade mark) surface active agent, and then, by adding physiological saline solution, a homogenous suspension was prepared for administration.

In order to compare its effect, bestatin was administered in a similar manner.

The experimental period was 60 days after transplantation of the tumor cells. The mean survival period in days until the death of the animal due to the tumor was calculated and then the increase in the mean survival period (survival rate) of the animals given only the anti-tumor chemotherapeutic agent and of the animals given the anti-tumor chemotherapeutic agent together with the test compound, over the mean survival period in days of the untreated control animals was calculated. The efficacy rate was additionally determined from the number of animals where the solid tumor diminished significantly, with or without metastasis, at the transplanted region within this experimental period.

The survival rate and efficacy rate of animals given the known agent carboquone together with the compound of the invention and the survival and efficacy rate of the animals given only carboquone were compared. In tests of this kind, it is commonly considered that a survival rate greater than 25 % indicates that a test compound has potentially valuable anti-tumor activity; accordingly, those groups showing a survival rate of 25% or more are evaluated as "+". Similarly, those groups were a 20% or greater increase in efficacy rate were noted are also evaluated as "+" (the efficacy rate of animals given carboquone alone was 0%). The results are shown in Table 6.

TABLE 6

| Compound No. | Increase in survival rate | Increase in efficacy rate |
|---|---|---|
| 1 | + | + |
| 2 | − | + |
| 6 | + | − |
| 7 | + | + |
| 8 | + | + |
| 10 | + | + |
| 13 | + | + |
| 11 | + | + |
| 16 | + | + |
| 60 | + | + |
| 97 | + | + |
| 98 | + | + |
| 115 | + | + |
| 117 | + | + |
| 118 | + | + |
| 119 | + | + |
| 127 | + | + |
| 128 | + | + |
| 133 | + | + |
| Bestatin | − | + |

The results shown in Table 6 indicate that the compounds of the invention significantly potentiate the activity of carboquone against the test tumors.

3. Anti-tumor activity against transplanted tumors $1 \times 10^5$ cells of mouse lymphoid leukemia L-1210 were transplanted to each of a group of mice (strain CDFI, supplied by Shizuoka Experimental Animal Farm). Adriamycin was administered intraperitoneally to the mice once a day for 3 consecutive days beginning the day following the transplantation. At the same time, the test compounds were administered orally to the mice once a day at a dosage of 0.1 mg/kg, 1.0 mg/kg or 10 mg/kg for 4 consecutive days beginning on the day following the administration and for a further five consecutive days beginning 7 days after the transplantation. The test preparations were prepared in the same manner as in the foregoing test. The test was carried out for 60 days, reckoning from the day of the transplantation. The mean number of days survival until death were calculated having regard to (a) a control group (no active compound administered), (b) an adriamycin group, and (c) adriamycin + test compound group, and the survival rates (b/a and c/a) were evaluated. Where the survival rate of the group (c) exceeded by 50% that of the group (b) at any of the dosages, the symbol "+" is given. The results are shown in the following Table 7.

TABLE 7

| Compound No. | Increase in survival rate vs. adriamycin group |
| --- | --- |
| 1 | + |
| 18 | + |
| 23 | + |
| 25 | + |
| 63 | + |
| Bestatin | + |

Accordingly, the compounds of the present invention have been shown to have an effect on the immune system, to have a beneficial effect on aquired immune deficiency and to be useful in the treatment of malignant tumors, either alone or in combination with another chemotherapeutic agent.

Accordingly, the compounds of the invention can be used as immunoregulatory agents for treatment of tumors, bacterial infections and auto-immune diseases. They may be administered orally (e.g. in the form of tablets, capsules, powders or granules) or non-orally (e.g. by means of subcutaneous, intravenous or intramuscular injection or as a suppository). The compounds may be formulated as conventional pharmaceutical compositions, containing any known pharmaceutically acceptable carriers, diluents or excipients and optionally other chemotherapeutic agents. The dose will vary, depending upon the condition, age and body weight of the patient, as well as upon the nature and severity of the disease and the times and routes of administration. However, in the case of an adult human patient, a dose of from 5 to 300 mg per day will normally be considered effective, and this may be administered in a single dose or in divided doses.

The compositions of the invention are preferably formulated in unit dosage form, each unit dose containing from 5 to 50 mg of the active ingredient or ingredients.

The invention is further illustrated by the following Examples. Preparation of certain of the starting materials employed in these Examples is given in the Preparations. In the Examples and Preparations, all optical rotations were measured using the sodium D-line, i.e. all are $[\alpha]_D$.

PREPARATION 1

Synthesis of N-(3-trifluoromethylbenzoyl)aminoacetic acid 5.5 of 3-trifluoromethylbenzoyl chloride were dropped slowly onto 15 ml of an aqueous solution containing 2.0 g of glycine and 2.1 g of sodium hydroxide, and then, after the dropwise addition was complete, the reaction solution was heated at 70° C. for 2 hours, with stirring. The mixture was allowed to stand to cool, and then the reaction solution was washed with ethyl acetate, the aqueous layer was neutralized with 8N hydrochloric acid, and the crystals which separated out were filtered to afford 4.6 g of the title compound, after drying.

Other intermediates of formula (VII) could also be synthesized in a similar manner.

PREPARATION 2

Synthesis of N-($\alpha,\alpha$-dimethylbenzyl)-3-(benzyloxycarbonylamino)-propionamide 6.6 g of N-benzyloxycarbonyl-$\beta$-alanine, 4.0 g of $\alpha,\alpha$-dimethylbenzylamine and 7.4 g of triethylamine were dissolved in 400 ml of anhydrous methylene chloride. To this solution were then added 8.8 g of 2-chloro-1-methylpyridinium iodide slowly at room temperature, and the mixture was heated under reflux for 2 hours. The reaction mixture was then washed, in turn, with a 10% w/v aqueous solution of sodium hydroxide, with a 1N aqueous solution of hydrochloric acid and with a saturated aqueous solution of sodium chloride, and was then dried over anhydrous sodium sulfate. The solution was concentrated by evaporation under reduced pressure, to give 10.7 g of crude crystals. Recrystallization of these from a mixture of hexane and benzene afforded 5.6 g (yield 56%) of the title compound melting at 96°–97° C.

PREPARATION 3

Synthesis of N-($\alpha,\alpha$-dimethylbenzyl)-3-aminopropionamide 1.5 g of palladium-on-carbon were suspended in a solution of 4.51 g of N-($\alpha,\alpha$-dimethylbenzyl)-3-(benzyloxycarbonylamino)propionamide (prepared as described in Preparation 2) in 110 ml of an 8:2:1 by volume mixture in methanol, acetic acid and water, and then hydrogen was passed through the solution for 4 hours at room temperature under normal atmospheric pressure. Undissolved materials were filtered off, the pH was adjusted to a value of 10 by the addition of a 10% w/v aqueous solution of sodium hydroxide, and then the mixture was extracted with 150 ml of ethyl acetate. The solution was washed with a saturated aqueous sodium chloride solution, dried over anhydrous sodium sulfate and concentrated by evaporation under reduced pressure to give 2.3 g of the title compound as an oil.

Other intermediates of formula (VIII) could also be synthesized in a similar manner.

PREPARATION 4

(2S)-N-(α,α-Dimethylbenzyl)-3-benzyloxy-2-(t-butoxycarbonylamino)propionamide 11.0 g of powdery N-(t-butoxycarbonyl)-O-benzyl-L-serine were added to 200 ml of a methylene chloride solution containing 5.0 g of α,α-dimethylbenzylamine and 10.0 g of triphenylphosphine. 20 ml of a methylene chloride solution containing 8.2 g of 2,2'-dipyridyl disulfide were then added dropwise. The mixture was then stirred for 1 hour at room temperature, after which the solvent was distilled off under reduced pressure and the residue was subjected to silica gel column chromatography. The title compound was obtained as an oil from the fraction eluted with a 2:1 by volume mixture of ethyl acetate and hexane. Yield 9.2 g.

PREPARATION 5

(2S)-N-(α,α-Dimethylbenzyl)-3-benzyloxy-2-aminopropionamide trifluoroacetate 15.09 g of trifluoroacetic acid were added to a solution of 9.0 g of (2S)-N-(α,α-dimethylbenzyl)-3-benzyloxy-2-(t-butoxycarbonylamino)propionamide (prepared as described in Preparation 4) in a mixture of 100 ml of methylene chloride and 2.4 g of anisole, and the whole mixture was stirred for 1 hour at room temperature. At the end of this time, the excess trifluoroacetic acid was distilled off. On adding diethyl ether, the residue gave 8.8 g of the title compound as needles melting at 148°–150° C.

PREPARATION 6

(2R)-N-(α,α-Dimethylbenzyl)-2-(t-butoxycarbonylamino)-3-(p-methoxybenzylthio)propionamide 12.51 g of N-t-butoxycarbonyl-S-(p-methoxybenzyl)-cysteine and then 8.57 g of 2,2'-dipyridyl disulfide were added to 150 ml of a methylene chloride solution containing 4.95 g α,α-dimethylbenzylamine and 9.69 g of triphenylphosphine. The solution was heated to reflux for 2.25 hours under a stream of nitrogen. At the end of this time, more methylene chloride was added. The methylene chloride layer was separated and washed with a cooled, dilute aqueous hydrochloric acid solution, with a 3% w/v ice-cooled aqueous solution of sodium hydroxide quickly, with a cooled, dilute hydrochloric acid solution and with a saturated aqueous sodium chloride solution, in that order. The methylene chloride layer was separated and dried over anhydrous sodium sulfate and the solvent was distilled off under reduced pressure. The residue (about 30 g) was purified by column chromatography using 500 g of silica gel. The fraction eluted with hexane containing 15–20% by volume of ethyl acetate afforded 15 g of a crystalline residue. Recrystallization of this residue from hexane containing ethyl acetate gave 13.3 g of the title compound melting at 81° C.

$[\alpha]^{25} = +6.7°$ (C=1.0, CHCl$_3$).

Infrared Absorption Spectrum (CHCl$_3$) $\nu_{max}$cm$^{-1}$: 1585, 1610, 1680, 3430.

Nuclear Magnetic Resonance Spectrum (CDCl$_3$) δ ppm: 1.47 (9H, singlet); 1.69 (6H, singlet); 2.75 (2H, doublet of doublets, J=5.8 and 9 Hz); 3.71 (2H, singlet); 3.78 (3H, singlet); 4.15 (1H, triplet, J=5.8 Hz); 6.8–7.5 (9H, multiplet).

PREPARATION 7

(2R)-N-(α,α-Dimethylbenzyl)-2-amino-3-(p-methoxybenzylthio)propionamide trifluoroacetate 1.6 g of thiophenol was added to 20 ml of a chloroform solution containing 6.093 g of (2R)-N-(α,α-dimethylbenzyl)-2-(t-butoxycarbonylamino)-3-(p-methoxybenzylthio)propionamide (prepared as described in Preparation 6), and then the mixture was placed over an ice-water bath, and 15 ml of trifluoroacetic acid were added; the mixture was stirred for 20 minutes at the temperature of the ice-water bath. After additional stirring for 1.5 hours at room temperature, the solvent and excess reagents were distilled off under reduced pressure. The residue obtained was dissolved in 7 ml of diethyl ether and addition of 50 ml hexane afforded the title compound.

PREPARATION 8

(2S)-N-(α,α-Dimethylbenzyl)-2-(t-butoxycarbonylamino)-6-benzyloxycarbonylaminohexanamide 517 mg of the dicyclohexylamine salt of N-t-butoxycarbonyl-N-benzyloxycarbonyllysine were dissolved in ethyl acetate containing a little water, and the solution was washed twice with a 10% w/v aqueous solution of citric acid. The ethyl acetate layer was separated and washed with water and with a saturated aqueous solution of sodium chloride and then dried over anhydrous magnesium sulfate. The solvent was distilled off, and the residue was dissolved in 9 ml of methylene chloride. 6 ml of a methylene chloride solution containing 209 mg of dicyclohexylcarbodiimide and 145 mg of α,α-dimethylbenzylamine were added to this solution and the mixture was stirred for 2.5 hours at room temperature, after which it was filtered. The filtrate was concentrated by evaporation under reduced pressure. The residue was dissolved in ethyl acetate and the solution was washed, in turn, with a 10% w/v aqueous solution of citric acid, a 5% w/v aqueous solution of sodium bicarbonate and a saturated aqueous solution of sodium chloride. The mixture was dried over anhydrous magnesium sulfate, and then the solvent was distilled off. The residue was subjected to silica gel column chromatography using a 1:1 by volume mixture of ethyl acetate and hexane as eluent, to give 297 mg of the title compound as an amorphous material.

Nuclear Magnetic Resonance Spectrum (CDCl$_3$) δ ppm: 1.05–1.86 (7H, multiplet); 1.43 (9H, singlet); 1.62, 1.64 (together 6H, each singlet); 3.11 (2H, broad doublet, J=6 Hz); 3.72–4.28 (1H, broad); 4.68–5.29 (3H, multiplet); 6.40–6.65 (1H, broad); 6.97–7.38 (10H, multiplet).

PREPARATION 9

(2S)-N-(α,α-Dimethylbenzyl)-2-amino-6-(benzyloxycarbonylamino)hexanamide

To 2.18 g of (2S)-N-(α,α-dimethylbenzyl)-2-(t-butoxycarbonylamino)-6-benzyloxycarbonylaminohexanamide (prepared as described in Preparation 8) were added 0.47 g of anisole and 10 ml of trifluoroacetic acid, and the solution was stirred for 30 minutes at room temperature. At the end of this time, the excess trifluoroacetic acid was distilled off under reduced pressure. A 5% w/v aqueous solution of sodium bicarbonate was added to the residue, and the mixture was neutralized and then extracted with ethyl acetate. The organic layer was extracted with a 10% w/v aqueous solution of citric acid. The aqueous extract was separated and neutralized with a 5% w/v aqueous solution of sodium bicarbonate and then extracted again with ethyl acetate. The extract was dried over anhydrous magnesium sulfate. After distilling off the solvent under reduced pressure, 1.01 g of the title compound was obtained as an amorphous material.

Nuclear Magnetic Resonance Spectrum (CDCl$_3$) δ ppm: 1.10–2.08 (7H, multiplet); 1.61, 1.64 (together 6H, each singlet); 3.11 (2H, broad doublet, J=5.8 Hz); 4.26–4.74 (1H, broad); 4.97–5.34 (3H, multiplet); 6.93–7.15 (1H, broad singlet); 7.15–7.56 (10H, multiplet); 7.77–8.12 (1H, multiplet).

PREPARATION 10

(1R,4R)-3-Benzoyl-1-oxothiazolidine-4-carboxylic acid and (1S,4R)-3-Benzoyl-1-oxothiazolidine-4-carboxylic acid (a) To a solution of 13.3 g of (4R)-3-benzoylthiazolidine-4-carboxylic acid [prepared as described in step (a) of Example 10] in 200 ml of methylene chloride were added, with ice-cooling, 4.96 g of chloromethyl methyl ether and 9.21 g of N,N-diethylaniline, and then the mixture was stirred at room temperature for 3 hours. The solvent was distilled off and the residue was dissolved in 150 ml of ethyl acetate. The solution was then washed, in turn, with 100 ml of water, 100 ml of a 0.5M aqueous solution of citric acid, 100 ml of water, 100 ml of a 4% w/v aqueous solution of sodium bicarbonate, and 100 ml of water.

The organic phase was dried and the solvent was distilled off to give 12.2 g of methoxymethyl (4R)-3-benzolythiazolidine-4-carboxylate.

Nuclear Magnetic Resonance Spectrum (CDCl$_3$) δ ppm: 2.25 (1H, singlet); 2.35 (1H, singlet); 3.44 (3H, singlet); 4.62 (2H, singlet); 5.29 (2H, singlet); 5.4–5.0 (1H, multiplet); 7.6–7.2 (5H, multiplet).

(b) The 12.2 g of methoxymethyl (4R)-3-benzoyl-thiazolidine-4-carboxylate, obtained as described in step (a) above, were dissolved in 300 ml of methylene chloride and then 8.36 g of 85% m-chloroperbenzoic acid were added whilst cooling at −5° C. The mixture was stirred at the same temperature for 30 minutes, after which it was washed, in turn, twice, each time with 300 ml of a 4% w/v aqueous solution of sodium bicarbonate and then with 100 ml of water, after which is was dried over anhydrous sodium sulfate. The mixture was concentrated by evaporation under reduced pressure, and the residue was purified by column chromatography through 450 g of silica gel, eluted with a 2.5:97.5 by volume mixture of ethanol and methylene chloride, to give 10.3 g of methoxymethyl (1RS,4R)-3-benzoyl-1-oxothiazolidine-4-carboxylate in the form of an oil.

(c) 10.2 g of the methoxymethyl 3-benzoyl-1-oxothiazolidine-4-carboxylate obtained as described in step (b) above were dissolved in a mixture of 25 ml of trifluoroacetic acid, 50 ml of methanol and 25 ml of water, and the solution was stirred at 40° C. for 3.5 hours. The solvent was then distilled off under reduced pressure, 100 ml of water were added to the residue, and then the water was distilled off under reduced pressure. 300 ml of diethyl ether were added to the resulting oily residue to give 5.80 g of a white powder, which was recrystallized from 200 ml of ethyl acetate to give crystals. The crystals were then subjected to fractional recrystallization to give 2.89 g of (1R, 4R)-3-benzoyl-1-oxothiazolidine-4-carboxylic acid melting at 203°–204° C. (with decomposition).

Infrared Absorption Spectrum (KBr) $v_{max}$cm$^{-1}$: 2990, 2930, 2610, 2500, 1730, 1630, 1600.

Mass spectrum (m/e): 253 (M+).

[α]$^{23}$ −358° (C=1.0 methanol).

Nuclear Magnetic Resonance Spectrum [(CD$_3$)$_2$SO] δppm: 3.21 (1H, doublet of doublets, J=9 and 14 Hz); 3.57 (1H, doublet of doublets, J=8 and 14 Hz); 4.52 (1H, doublet, J=10 Hz); 4.74 (1H, doublet, J=10 Hz); 5.33 (1H, doublet of doublets, J=8 and 9 Hz); 7.59 (5H, singlet).

(d) To the alcoholic mother liquor, from which fractional recrystallization had been effected in step (c), a small excess of dicyclohexylamine was added, and then the mixture was allowed to stand at room temperature for 2 hours. The crystals which precipitated were recrystallized from ethanol to give 3.95 g of dicyclohexylammonium (1S,4R)-3-benzoyl-1-oxothiazolidine-4-carboxylate, melting at 186°–198° C. (with decomposition). 3.0 g of the cyclohexyl amine salt thus obtained were dissolved in 50 ml of 50% v/v aqueous ethanol, and the solution was passed through a column containing 50 ml of a cation-exchange resin (Dowex 50H+, trade mark), and eluted with 50% v/v aqueous ethanol. The solvent was distilled off and the residue was recrystallized from a 1:3 by volume mixture of ethanol and diethyl ether, to give 1.54 g of (1S,4R)-3-benzoyl-1-oxothiazolidine-4-carboxylic acid melting at 174°–175° C. (with decomposition).

Infrared Absorption Spectrum (KBr) $v_{max}$cm$^{-1}$: 2920, 2590, 1725, 1645.

Mass Spectrum (m/e): 253 (M+).

[α]$^{23}$ −87.2° (C=1.0, methanol).

Nuclear Magnetic Resonance Spectrum [(CD$_3$)$_2$SO] δ ppm: 3.37 (1H, singlet); 3.44 (1H, doublet of doublets, J×9 and 13.5 Hz); 4.28 (1H, doublet, J=12 Hz); 5.11 (1H, doublet, J=12 Hz); 5.27 (1H, broad singlet); 7.55 (5H, singlet).

PREPARATION 11

Methoxymethyl (4R)-3-benzoyl-1,1-dioxothiazolidine-4-carboxylate 79.3 g (0.390 mole) of 85% m-chloroperbenzoic acid were added to a solution of 50.0 g (0.177 mole) of methoxymethyl (4R)-3-benzoylthiazolidine-4-carboxylate [prepared as described in step (a) of Preparation 10] in 500 ml of methylene chloride cooled at 5° C., and then the mixture was stirred at a temperature from 5° to 8° C. for 30 minutes and then at room temperature for a further 24 hours. The reaction mixture was filtered, the filtered solid was washed with 200 ml of methylene chloride, and the filtrate and the washings were combined and concentrated by evaporation under reduced pressure to a volume of about 400 ml. The concentrate was washed three times, each time with 400 ml of a 4% w/v aqueous solution of sodium bicarbonate and dried over anhydrous magnesium sulfate. The solvent was then distilled off under reduced pressure.

The crystalline residue was recrystallized from a 9:1 by volume mixture of diethyl ether and methylene chloride to give 36.3 g (65.5%) of the title compound in the form of colorless needles melting at 80°–81° C.

[α]$^{23}$ −122.2° (C=1.0, methanol).

Elemental Analysis: Calculated: C, 49.83%; H, 4.83%; N, 4.47%; S, 10.23%. Found: C, 49.94%; H, 4.84%; N, 4.51%; S, 10.16%.

Infrared Absorption Spectrum (KBr) $v_{max}$cm$^{-1}$: 1731, 1638.

Nuclear Magnetic Resonance Spectrum (CDCl$_3$) δ ppm: 3.50 (3H, singlet); 3.58 (2H, doublet, J=6.0 Hz); 4.49 (1H, AB-doublet, J=12.0 Hz); 4.70 (1H, AB-doublet, J=12.0 Hz); 5.36 (2H, singlet); 5.66 (1H, triplet, J=6.0 Hz); 7.53 (5H, singlet).

PREPARATION 12

(4R)-3-Benzoyl-1,1-dioxothiazolidine-4-carboxylic acid 31.3 g of methoxymethyl (4R)-3-benzoyl-1,1-dioxothiazolidine-4-carboxylate (prepared as described in Preparation 11) were dissolved in 200 ml of a 1:1 by volume mixture of trifluoroacetic acid and water, and then the mixture was stirred at room temperature for 1 hour. The reaction mixture was then concentrated by evaporation under reduced pressure to leave crystals. These crystals were washed with 150 ml of water and then recrystallized from ethyl acetate to give 21.6 g (80.3%) of the title compound in the form of colorless needles melting at 175°-176° C.

$[\alpha]^{22}$ −133.0° (C=1.0, methanol).

Elemental Analysis: Calculated: C, 49.07%; H, 4.12%, N, 5.20%; S, 11.91%. Found: C, 48.93%; H, 4.03%; N, 5.10%, S, 12.05%.

Infrared Absorption Spectrum (KBr) $v_{max}$cm$^{-1}$: 3600-2300, 1759.

Nuclear Magnetic Resonance Spectrum [(CD$_3$)$_2$SO] δ ppm: 3.63 (1H, AB-doublet of doublets, J=13.5 and 5.4 Hz); 3.93 (1H, AB-doublet of doublets, J=13.5 and 9.0 Hz); 4.60 (1H, AB-doublet, J=12.0 Hz); 4.82 (1H, AB-doublet, J=12.0 Hz); 5.31 (1H, doublet of doublets, J=5.4 and 9.0 Hz); 7.56 (5H, singlet).

PREPARATION 13

(R)-α-Methyl-p-hydroxybenzylamine (a) 115.2 g (1.405 moles) of sodium acetate, 108.9 g (0.800 mole) of p-hydroxyacetophenone and 1000 ml of ethanol were added to a solution of 56.8 g (0.817 mole) of hydroxylamine hydrochloride in 1000 ml of water, and then the mixture was refluxed for 4 hours. At the end of this time, the reaction mixture was concentrated by evaporation under reduced pressure to a volume of about 500 ml, and the concentrate was allowed to cool at room temperature for 23 hours to precipitate crystals. The crystals were washed with 500 ml of water, and dried in air for 24 hours and in vacuo for a further 6 hours to give 102.1 g (84.5%) of p-hydroxyacetophenone oxime in the form of colorless needles melting at 145°-146°.

(b) 10.0 g of 10% w/w palladium-on-charcoal were added to a solution of 50.0 g (0.33 mole) of p-hydroxyacetophenone oxime [prepared as described in step (a) above] in 400 ml of acetic acid, and the mixture was subjected top catalytic hydrogenation for 8 hours. The catalyst was filtered off, the filtered solid was washed with 100 ml of acetic acid, and the filtrate and the washings were combined and concentrated by evaporation under reduced pressure. The residue was dissolved in 400 ml of water, washed with 400 ml of ethyl acetate and then adjusted to a pH value of 10.10 by the addition of a 20% w/v aqueous solution of sodium hydroxide, whilst cooling at a temperature between 5° and 10° C. the crystals which precipitated were collected by filtration, and washed, in turn, with 100 ml of cold water and 200 ml of acetone, to give 29.2 g (64.6%) of (R,S)-α-methyl-p-hydroxybenzylamine in the form of a colorless powder melting at 124°-126° C.

(c) 137.1 g (1.0 mole) of (R,S)-α-methyl-p-hydroxybenzylamine [prepared as described in step (b) above] were added to 500 ml of an aqueous solution containing 134.0 g (1 mole) of L-malic acid, and then the mixture was stirred at room temperature for 15 minutes. At the end of this time, the solvent was distilled off under reduced pressure to leave crystals. The crystals were washed with 500 ml of ethanol and then subjected to fractional recrystallization from water (3 times) to give 76.2 g (56.2%) of (R)-α-methyl-p-hydroxybenzylamine L-malate in the form of colorless prisms melting at 166°-167° C.

(d) 277 ml of a cooled 20% w/v aqueous solution of sodium hydroxide were added dropwise to 75.2 g (0.277 mole) of (R)-α-methyl-p-hydroxybenzylamine L-malate [obtained as described in step (c) above], and then the mixture was stirred at a temperature between 2° and 5° C. for 15 hours. At the end of this time, 60 g of sodium chloride were added, and the whole mixture was stirred at a temperature between 2° and 5° C. for a further 15 minutes. The crystals which precipitated were collected by filtration, and washed in turn with 100 ml of cold water and 100 ml of acetone to give 32.3 g (85.2%) of the title compound in the form of a colorless powder melting at 124°-125° C.

$[\alpha]^{23}$ +23.6° (C=1.0, methanol).

PREPARATION 14

(4R)-4-[(R)-α-Methylbenzylcarbamoyl]thiazolidine 20.22 g (0.20 mole) of triethylamine were added dropwise to a suspension of 26.62 g (0.20 mole) of (4R)-thiazolidine-4-carboxylic acid in 200 ml of a 1:1 by volume mixture of water and dioxane, whilst cooling at 5° C., and then a solution of 48.00 g (0.22 mole) of di-t-butoxy dicarbonate in 10 ml of dioxane was added dropwise. After completion of the addition, the mixture was stirred at a temperature between 0° and 5° C. for 30 minutes, and then at room temperature for a further 20 hours. At the end of this time, 200 ml of water were added to the reaction mixture, which was then washed with 300 ml of ethyl acetate. The aqueous layer was separated and it was then neutralised by the addition of 50 g of citric acid. The mixture was extracted twice, each time with 300 ml of ethyl acetate, and the extract was dried over anhydrous magnesium sulfate. The solvent was distilled off under reduced pressure and the residue was crystallized by the addition of diisopropyl ether to give 41.20 g (88.3%) of (4R)-3-t-butoxycarbonylthiazolidine-4-carboxylic acid in the form of colorless needles melting at 133°-134° C.

10 g (42.8 mmole) of this compound were dissolved in 200 ml of methylene chloride and, whilst cooling at 5° C. 5.20 g (42.8 mmole) of (R)-α-methylbenzylamine, 5.80 g (42.8 mmole) of N-hydroxybenzotriazole and 8.85 g (42.8 mmole) of dicyclohexylcarbodiimide were added in that order to the solution. The mixture was stirred at a temperature between 0° and 5° C. for 30 minutes, and then at room temperature for a further 4 hours, after which it was filtered to remove the insoluble matter. These insolubles were washed with 50 ml of methylene chloride. The filtrate and the washings were combined, and washed, in turn, with 200 ml of a 10% w/v aqueous solution of potassium dihydrogen phosphate and 200 ml of a 10% w/v aqueous solution of dipotassium hydrogen phosphate. The organic phase was separated and dried over anhydrous magnesium sulfate, and the solvent was distilled off under reduced pressure. The residue was purified by Lobar column chromatography (Merck, Art 10402), eluted with a 4:1 by volume mixture of cyclohexane and ethyl acetate, and then crystallized by the addition of diisopropyl ether to give 10.30 g (71.5%) of (4R)-3-t-butoxycarbonyl-4-[(R)-α-methylbenzylcarbamoyl]thiazolidine in the form of colorless needles melting at 105°–106° C.

$[\alpha]^{23}$ −42.2° (C=1.0, methanol).

6.73 g (20.0 mmole) of this compound were dissolved in 60 ml of methylene chloride and, whilst cooling at 5° C., 15 ml of trifluoroacetic acid were added to the solution. The mixture was stirred at a temperature between 0° and 5° for 30 minutes, and then at room temperature for a further 7 hours. At the end of this time, the solvent was distilled off under reduced pressure from the reaction mixture and the residue was dissolved in 200 ml of ethyl acetate. The solution was washed with 200 ml of a 4% w/v aqueous solution of sodium bicarbonate and then dried over anhydrous magnesium sulfate. The solvent was distilled off under reduced pressure and the residue was purified by silica gel Lobar column chromatography (Merck, Art 10402), eluted with a 1:1 by volume mixture of cyclohexane and ethyl acetate and then crystallized by the addition of diisopropyl ether to give 4.20 g (89.3%) of the title compound in the form of a colorless powder melting at 84°–85° C.

$[\alpha]^{23}$ +42.7° (C=1.0, methanol).

Elemental Analysis: Calculated for $C_{12}H_{16}N_2OS$: C, 60.99%; H, 6.82%; N, 11.85%; S, 13.57%. Found: C, 61.15%; H, 6.75%; N, 11.90%; S, 13.56%.

Infrared Absorption Spectrum (KBr) $\nu_{max}cm^{-1}$: 3275, 1650 (shoulder), 1639.

Nuclear Magnetic Resonance Spectrum (CDCl$_3$) δ ppm: 1.49 (3H, doublet, J=7.5 Hz); 2.16–2.63 (1H, broad); 3.08 (1H, AB-doublet of doublets, J=11.7 and 7.5 Hz); 3.41 (1H, AB-doublet of doublets, J=11.7 and 4.5 Hz); 3.87 (1H, AB-doublet, J=9.0 Hz); 4.10 (1H, doublet of doublets, J=7.5 and 4.5 Hz); 4.16 (1H, AB-doublet, J=9.0 Hz); 5.11 (1H, quartet of doublets, J=7.5 and 7.5 Hz); 7.33 (5H, singlet).

EXAMPLE 1

N-(α,α-Dimethylbenzyl)-2-benzoylaminoacetamide (Compound No. 1)

1.0 g of α,α-dimethylbenzylamine and 1.95 g of triphenylphosphine were dissolved in 100 ml of anhydrous methylene chloride. 1.33 g of hippuric acid and 1.63 g of 2,2′-dipyridyl disulfide were added in that order to the solution, and the mixture was heated under reflux for 2 hours. At the end of this time, the reaction solution was washed with a 10% w/v aqueous solution of sodium hydroxide and then with 1N aqueous hydrochloric acid, and dried over anhydrous sodium sulfate After concentration of the reaction solution by evaporation under reduced pressure, the resulting residue was subjected to silica gel column chromatography for separation and purification (using as eluent a 1:1 by volume mixture of hexane and ethyl acetate), to give 1.97 g (yield 90%) of the title product melting at 156°–157° C.

Elemental Analysis: Calculated for $C_{18}H_{20}N_2O_2$: C, 72.95%, H, 6.80%, N, 9.45%. Found: C, 72.99%, H, 6.89%, N, 9.45%.

Infrared Absorption Spectrum (Nujol-trade markmull) $\nu_{max}cm^{-1}$: 3380, 3280, 1680, 1645.

Nuclear Magnetic Resonance Spectrum (CDCl$_3$) δ ppm: 1.72 (6H, singlet); 4.21 (2H, doublet, J=5 Hz); 7.2–7.7 (10H, multiplet); 7.8–8.0 (2H, multiplet).

EXAMPLE 2

Synthesis of N-(1,2,2-Trimethylpropyl)-2-benzoylaminoacetamide 2.2 g of dicyclohexylcarbodiimide were added to 30 ml of an ethyl acetate solution containing 1.0 g of 3-amino-2,2-dimethylbutane and 1.7 g of hippuric acid in an ice bath. The reaction solution was stirred for 2 hours at room temperature and then allowed to stand overnight. The solid material which separated was filtered off, after which the filtrate was washed with a 10% w/v aqueous solution of sodium hydroxide, then with 1N aqueous hydrochloric acid, and finally with a saturated aqueous sodium chloride solution. It was then dried over anhydrous sodium sulfate. The reaction solution was concentrated by evaporation under reduced pressure, and the resulting residue was purified by silica gel column chromatography to give 1.65 g (yield 64%) of the title product melting at 124°–126° C.

Elemental analysis: Calculated for $C_{15}H_{22}N_2O_2$: C, 68.67%; H, 8.45%; N, 10.68%. Found: C, 68.65%, H, 8.60%, N, 10.65%.

Infrared Absorption Spectrum (Nujol mull) $\nu_{max}cm^{-1}$: 3300, 1680, 1640.

Nuclear Magnetic Resonance Spectrum (CDCl$_3$) δ ppm: 0.90 (9H, singlet); 1.09 (3H, doublet, J=7 Hz); 3.80 (1H, quartet of doublets, J=7 and 3 Hz); 4.18 (2H, doublet, J=7 Hz); 6.9–7.1 (1H, broad singlet); 7.3–7.55 (3H, multiplet); 7.65–8.0 (3H, multiplet).

EXAMPLE 3

Synthesis of N-(α-methylbenzyl)-2-(2,6-dichlorobenzoylamino)acetamide (Compound No. 74)

1.05 g of isobutyl chloroformate was slowly dropped at −20° C. under a nitrogen stream onto a solution of 1.74 g of N-(2,6-dichlorobenzoyl)glycine and 0.71 g of triethylamine in 30 ml of anhydrous tetrahydrofuran, and the reaction solution was stirred for 20 minutes. Then, 0.84 g of α-phenylethylamine was added to the solution, which was subsequently stirred for 30 minutes keeping the reaction temperature within the range from −10° C. to −20° C. The reaction solution was then extracted with 60 ml of ethyl acetate. The extract was washed with a 10% w/v aqueous solution of sodium hydroxide, then with 1N aqueous hydrochloric acid, and finally with a saturated aqueous solution of sodium chloride, and was then dried over anhydrous sodium sulfate. The reaction solution was concentrated by evaporation under reduced pressure, and the resulting residue was subjected to silica gel column chromatography for purification to give 1.58 g (yield 67%) of the title product melting at 155° C.

Elemental analysis: Calculated for $C_{17}H_{16}N_2O_2Cl_2$: C, 58.13%; H, 4.59%; N, 7.9%; Cl, 20.19%. Found: C, 57.98%; H, 4.68%; N, 8.02%, Cl 20.34%.

Infrared Absorption Spectrum (Nujol mull) $\nu_{max}cm^{-1}$: 3340, 3230, 1645.

Nuclear Magnetic Resonance Spectrum [(CD$_3$)$_2$SO] δ ppm: 1.40 (3H, doublet, J=7 Hz); 3.87 (2H, doublet, J=6 Hz); 4.90 (1H, quartet of doublets, J=7 and 6 Hz); 7.07–8.87 (10H, multiplet).

EXAMPLE 4

Synthesis of N-(α,α-dimethylbenzyl)-3-(benzoylamino)propionamide (Compound No. 3).

0.3 g of benzoyl chloride was slowly dropped onto 10 ml of a toluene solution containing 0.4 g of N-(α,α-dimethylbenzyl)-3-aminopropionamide (prepared as described in Preparation 3) and 0.22 g of triethylamine. The reaction solution was then stirred for 2 hours, and, after dilution with 20 ml of diethyl ether, was washed with water and dried over anhydrous sodium sulfate. The reaction solution was then concentrated by evaporation under reduced pressure, and purified by silica gel chromatography, to give 0.52 g (yield 87%) of the title compound melting at 147°–148° C.

Elemental analysis: Calculated for $C_{19}H_{22}N_2O_2$: C, 73.52%; H, 7.14%; N, 9.02%. Found: C, 72.92%; H, 7.15%; N, 9.02%.

Infrared Absorption Spectrum (Nujol mull) $\nu_{max}$cm$^{-1}$: 3300, 1640.

Nuclear Magnetic Resonance Spectrum (CDCl$_3$) δ ppm: 1.69 (6H, singlet); 2.54 (2H, triplet, J=6 Hz); 3.71 (2H, triplet of doublets, J=6 and 6 Hz); 7.2–7.6 (10H, multiplet); 7.7–8.0 (2H, multiplet).

EXAMPLE 5

(2S)-N-(α,α-Dimethylbenzyl)-2-benzoylamino-3-benzyloxypropionamide (Compound No. 13)

3.2 g of an oily substance [which had been obtained by the treatment of the (2S)-N-(α,α-dimethylbenzyl)-3-benzyloxy-2-aminopropionamide trifluoroacetate (prepared as described in Preparation 5) with triethylamine] were dissolved, together with 1.5 g of triethylamine, in 150 ml of methylene chloride. 1.5 g of benzoyl chloride was dropped onto this solution in an ice bath, and the reaction solution was stirred for 30 minutes, after which the methylene chloride layer was separated, washed with water and dried over anhydrous sodium sulfate. The solvent was distilled off and recrystallization of the residue from a mixture of diethyl ether and hexane gave 4.1 g of the title compound melting at 88°–90° C.

Elemental analysis: Calculated for $C_{26}H_{28}N_2O_3$: C, 74.97%; H, 6.87%; N, 6.73%. Found: C, 74.74%; H, 6.85%; N, 6.68%.

Infrared Absorption Spectrum (Nujol mull) $\nu_{max}$cm$^{-1}$: 3250, 1660, 1630.

EXAMPLE 6

(2S)-N-(α,α-Dimethylbenzyl)-3-hydroxy-2-(benzoylamino)propionamide (Compound No. 14)

2.0 g of (2S)-N-(α,α-dimethylbenzyl)-2-benzoylamino-3-benzyloxypropionamide (prepared as described in Example 5) was catalytically reduced with hydrogen gas in the presence of 0.4 g of 10% w/w palladium-on-carbon in a mixture of 4 ml of acetic acid and 60 ml of ethanol. After completion of the reaction, the catalyst was filtered off and the solvent was distilled off. Recrystallization of the resulting residue from acetic acid and hexane gave 1.4 g of the title compound, melting at 152°–153° C.

Elemental analysis: Calculated for $C_{19}H_{22}N_2O_3$: C, 69.92%; H, 6.79%; N, 8.58%. Found: C, 70.03%; H, 6.87%; N, 8.66%.

Infrared Absorption Spectrum (Nujol mull) $\nu_{max}$cm$^{-1}$: 3400, 3350, 1660, 1630.

EXAMPLE 7

(2R)-N-(α,α-Dimethylbenzyl)-2-benzoylamino-3-mercaptopropionamide (Compound No. 18)

(a)

(2R)-N-(α,α-Dimethylbenzyl)-2-benzoylamino-3-(p-methoxybenzylthio)propionamide 13.3 g of (2R)-N-(α,α-dimethylbenzyl)-2-(t-butoxycarbonylamino)-3-(p-methoxybenzylthio)propionamide (prepared as described in Preparation 6) were dissolved in 50 ml of toluene. To this solution were added 4.70 ml of triethylamine, and then 2.23 g of benzoyl chloride was added slowly to the mixture, whilst ice-cooling. The reaction solution was stirred for 70 minutes, and then ethyl acetate was added to it, after which it was washed with a saturated aqueous solution of sodium chloride and dried over anhydrous sodium sulfate. The solvent was distilled off and the resulting residue was purified by column chromatography through 210 g of silica gel. From the fraction eluted with hexane containing 30–40% v/v ethyl acetate, were obtained 4.31 g of an oily substance. This substance was dissolved in a mixture of ethyl acetate and hexane, and, after removal of crystals which had separated out (about 250 mg, melting at 189° C.), concentration of the mother liquor gave 3.61 g of the title compound as a glassy substance, $[\alpha]^{25} = -25.3°$ (C=1, CHCl$_3$).

Infrared Absorption Spectrum (CHCl$_3$) $\nu_{max}$cm$^{-1}$: 1581, 1611, 1650, 1680, 3330 3420.

Nuclear Magnetic Resonance Spectrum (CDCl$_3$) δ ppm: 1.68 (6H, singlet); 2.6–3.2 (2H, multiplet); 3.77 (2H, singlet); 3.81 (3H, singlet); 4.75 (1H, multiplet); 6.7–7.9 (16H, multiplet).

Mass spectrum (m/e): 462 (M+).

(b)

(2R)-N-(α,α-Dimethylbenzyl)-2-benzoylamino-3-mercaptopropionamide 1.010 g of (2R)-N-(α,α-dimethylbenzyl)-2-benzoylamino-3-(p-methoxybenzylthio)propionamide [prepared as described in step (a) above] was dissolved in 10 ml of trifluoroacetic acid. To this solution was added 1.0 ml of anisole and, whilst ice-cooling, this was followed by the addition of 793 mg of mercuric acetate under a nitrogen stream, and then the mixture was stirred. After stirring for 1.5 hours, the solvent was distilled off at room temperature. Diethyl ether was added to the residue and the material which separated out was filtered off. This material obtained by filtration (the mercuric salt) was dissolved in 50 ml of dimethylformamide, and, whilst ice-cooling, hydrogen sulfide gas was passed through this solution. After 1.5 hours, the mercuric sulfide which separated out was filtered off with Celite (trade mark) filter aid. The filtrate was concentrated by evaporation under reduced pressure at room temperature to give 702 mg of the title compound as crystals melting at 169°–173° C.

Infrared Absorption Spectrum (CHCl$_3$) $\nu_{max}$cm$^{-1}$: 1585, 1607, 1650, 1680, 3330, 3430.

Nuclear Magnetic Resonance Spectrum (CDCl$_3$) δ ppm: 1.68 (6H, singlet); 2.7–3.3 (2H, multiplet); 4.90 (1H, multiplet): 7.1–8.0 (10H, multiplet), Mass spectrum (m/e): 342 (M+), (M+ +1). EXAMPLE 8

(2S)-N-(α,α-Dimethylbenzyl)-2-benzoylamino-6-benzyloxycarbonylaminohexanamide (Compound No. 19)

To 80 ml of a methylene chloride solution containing 2.14 g of (2S)-N-(α,α-dimethylbenzyl)-2-amino-6-(benzyloxycarbonylamino)hexanamide (prepared as described in Preparation 9) and 0.51 g of pyridine were added dropwise, whilst ice-cooling, 30 ml of a methylene chloride solution containing 0.76 g benzoyl chloride, over a period of 10 minutes, with stirring. The mixed solution was stirred for a further 1.5 hours at room temperature, and then the solvent was distilled off. The residue was dissolved in ethyl acetate containing a small amount of water. A 10% w/v aqueous solution of citric acid was added, and then the solution was extracted with ethyl acetate. The extract was washed with a 5% w/v aqueous solution of sodium bicarbonate and then with a saturated aqueous solution of sodium chloride, after which it was dried over anhydrous sodium sulfate. The solvent was distilled off under reduced pressure, and the resulting residue was subjected to silica gel column chromatography. The fraction eluted with a 1:1 by volume mixture of ethyl acetate and hexane gave 2.06 g of the title compound as an amorphous substance melting at 53°–58° C. (with decomposition)

Elemental analysis: Calculated for $C_{30}H_{35}N_3O_4$: C, 71.83%; H, 7.03%; N, 8.38%. Found: C, 71.28%; H, 6.83%; N, 8.29%.

Infrared Absorption Spectrum (Nujol mull) $\nu_{max}$cm$^{-1}$: 3280, 1720, 1700, 1655, 1635.

Nuclear Magnetic Resonance Spectrum (CDCl$_3$) δ ppm: 0.95–2.10 (6H, multiplet); 1.60 (6H, broad singlet); 3.12 (2H, broad doublet, J=5.8 Hz); 4.53–5.30 (4H, multiplet); 6.91–7.93 (17H, multiplet).

EXAMPLE 9

(2S)-N-(α,α-Dimethylbenzyl)-6-amino-2-benzoylaminohexanamide (Compound No. 20)

1.73 g of (2S)-N-(α,α-dimethylbenzyl)-2-benzoylamino-6-(benzyloxycarbonylamino)hexanamide (prepared as described in Example 8) dissolved in 80 ml of ethanol and 4 ml of 1N hydrochloric acid was catalytically reduced by hydrogen gas in the presence of 0.33 g of 10% w/w palladium-on-carbon at room temperature. After filtering off the catalyst, the filtrate was concentrated by evaporation under reduced pressure to afford 1.35 g of the title compound as an amorphous substance melting at 94°–101° C. (with decomposition)

Elemental analysis: Calculated for $C_{22}H_{29}N_3O_2 \cdot HCl \cdot \frac{1}{3} H_2O$: C, 64.46%; H, 7.54%; N, 10.25%. Found: C, 64.11%; H, 7.70%; N, 9.92%.

Infrared Absorption Spectrum (Nujol mull) $\nu_{max}$cm$^{-1}$: 3250, 1655, 1635.

By following the procedures described in the foregoing Examples, but employing appropriate starting materials, the following compounds were prepared. The compounds are identified by the numbers assigned to them in Tables 1–4.

Compound No. 2 melting at 128°–129° C.
Compound No. 4 melting at 189°–190° C.
Compound No. 5 melting at 133°–134° C.
Compound No. 6 melting at 165°–167° C.
Compound No. 7 melting at 150°–152° C.
Compound No. 8 melting at 128°–129° C.
Compound No. 9 melting at 149°–151° C.
Compound No. 10 melting at 162°–164° C.
Compound No. 11 melting at 167°–168° C. Compound No. 12 melting at 216°–216.5° C.
Compound No. 15 melting at 181°–182° C.
Compound No. 16 melting at 98°–100° C.
Compound No. 17 melting at 128°–130° C.
Compound No. 21, an amorphous powder
Compound No. 22 melting at 143°–144° C.
Compound No. 23 melting at 73°–75° C.
Compound No. 24 melting at 108°–110° C.
Compound No. 25 melting at 181°–182° C.
Compound No. 26 melting at 199°–200° C.
Compound No. 27 melting at 148°–150° C.
Compound No. 29 melting at 168°–169° C.
Compound No. 30 melting at 141°–142° C.
Compound No. 31 melting at 169° C.
Compound No. 32 melting at 150°–151° C.
Compound No. 33 melting at 132°–133° C.
Compound No. 34 melting at 137° C.
Compound No. 35 melting at 176° C.
Compound No. 36 melting at 180° C.
Compound No. 37 melting at 163°–164° C.
Compound No. 38, an amorphous powder
Compound No. 39 melting at 143°–144° C.
Compound No. 40 melting at 73°–75° C.
Compound No. 41 melting at 108°–111° C.
Compound No. 54 melting at 138°–139° C.
Compound No. 55 melting at 128°–129° C.
Compound No. 56 melting at 155°–156° C.
Compound No. 57 melting at 124°–125° C.
Compound No. 58 melting at 127°–129° C.
Compound No. 59 melting at 183°–186° C.
Compound No. 60 melting at 205° C.
Compound No. 61 melting at 201°–202° C.
Compound No. 62 melting at 201°–204° C.
Compound No. 63 melting at 190°–192° C.
Compound No. 64 melting at 193° C.
Compound No. 65 melting at 185°–187° C.
Compound No. 66 melting at 153°–155° C.
Compound No. 67 melting at 185°–189° C.
Compound No. 68 melting at 145° C.
Compound No. 69 melting at 173°–174° C.
Compound No. 70 melting at 145°–147° C.
Compound No. 71 melting at 149°–154° C.
Compound No. 72 melting at 62° C.
Compound No. 73 melting at 119°–121° C.
Compound No. 75 melting at 182° C.
Compound No. 76 melting at 179°–180° C.
Compound No. 77 melting at 179°–180° C.
Compound No. 78 melting at 156°–157° C.
Compound No. 79 melting at 180°–183° C.
Compound No. 80 melting at 178°–180° C.
Compound No. 82 melting at 122°–124° C.
Compound No. 83 melting at 152°–153° C.
Compound No. 84 melting at 122°–124° C.
Compound No. 85 melting at 152°–153° C.
Compound No. 97, a gum
Compound No. 98, a gum
Compound No. 133, a gum
Compound No. 136 melting at 119°–120° C.

EXAMPLE 10

(4R)-3-Benzoyl-4-[(R)-α-methylbenzylcarbamoyl]-thiazolidine (Compound No. 115)

(a) 1 liter of acetone was added to a solution of 266.2 g of (4R)-thiazolidine-4-carboxylic acid in 1 liter of a 2N aqueous solution of sodium hydroxide. The solution was cooled at a temperature between 2° and 5° C., and then a solution of 280 g of benzoyl chloride in 0.8 liter of acetone was added dropwise, while maintaining the pH value of the reaction mixture at 7.5-8.0 by the addition of 1 liter of a 2N aqueous solution of sodium hydroxide. When the addition was complete, the reaction mixture was stirred at a temperature between 0° and 5° C. for 1 hour, after which it was concentrated by evaporation under reduced pressure to a volume of about 2.5 liters. The concentrate was washed with 2 liters of ethyl acetate, the aqueous phase was adjusted to a pH value of 2.0 by the addition of concentrated hydrochloric acid, maintaining the temperature at between 0° and 5° C., and the mixture was extracted twice, each time with 2 liters of ethyl acetate. The ethyl acetate phase was washed with a 10% w/v aqueous solution of sodium chloride and dried over anhydrous magnesium sulfate. The solvent was then distilled off to give 511.2 g of (4R)-3-benzoylthiazolidine-4-carboxylic acid.

(b) The whole of the compound prepared as described in step (a) above was dissolved in 3 liters of methylene chloride. 275.9 ml of triethylamine were added to the solution at −30° C., and then 270.5 g of isobutyl chloroformate were added dropwise. The mixture was stirred at a temperature between −40° C. and −30° C., for 1 hour, after which 212.2 g of (R)-α-methylbenzylamine were added dropwise at the same temperature.

The mixture was stirred for 30 minutes and then washed, in turn, with 1 liter of a 10% w/v aqueous solution of sodium chloride, 1 liter of 0.1N aqueous hydrochloric acid, a 10% w/v aqueous solution of sodium chloride, a 4% w/v aqueous solution of sodium carbonate and a 10% w/v aqueous solution of sodium chloride. The organic phase was dried over anhydrous magnesium sulfate and the solvent was distilled off under reduced pressure. The residue was dissolved in 3 liters of a 1:1 by volume mixture of methylene chloride and diethyl ether, and the solution was treated with 35 g of activated carbon. The solvent was distilled off to give an oil, to which 3 liters of diethyl ether was added, affording 515 g of the title compound in the form of colorless prisms melting at 111°-112° C.

$[\alpha]^{24}$ −99.8° (C=1.0, methanol).

Elemental analysis: Calculated for $C_{19}H_{20}N_2O_2S$: C, 67.03%; H, 5.92%; N, 8.23%; S, 9.42%. Found: C, 67.03%; H, 6.00%; N, 8.23%; S, 9.39%.

Infrared Absorption Spectrum (KBr) $\nu_{max}$cm$^{-1}$: 3350, 1661 (shoulder), 1643.

Nuclear Magnetic Resonance Spectrum (CDCl$_3$) δ ppm: 1.49 (3H, doublet, J=7.0 Hz); 3.18 (1H, doublet of doublets, J=12 and 7.5 Hz); 3.69 (1H, doublet of doublets, J=12 and 6 Hz); 4.37 (1H, doublet, J=10 Hz); 4.63 (1H, doublet, J=10 Hz); 4.9-5.3 (1H, broad); 5.13 (1H, quintet, J=7 Hz); 7.0-7.7 (1H, broad); 7.30 (5H, singlet); 7.46 (5H, singlet).

EXAMPLES 11-24

The procedure of Example 10 was followed, except that 4R, 4S or 4RS thiazolidine-4-carboxylic acid and R, S or RS α-methylbenzylamine or other corresponding compounds were used, to give the following compounds.

(4R)-3-Benzoyl-4-[(S)-α-methylbenzylcarbamoyl]-thiazolidine (Compound No. 116)

Melting Point: 121°-122° C.
$[\alpha]^{24}$ −296.1° (C=1.0, methanol).
Infrared Absorption Spectrum (KBr) $\nu_{max}$cm$^{-1}$: 3400, 3350, 1675, 1662, 1640, 1625.

Nuclear Magnetic Resonance Spectrum (CDCl$_3$) δ ppm: 1.47 (3H, doublet, J=7 Hz); 3.16 (1H, doublet of doublets, J=12 and 7.5 Hz); 3.49 (1H, doublet of doublets, J=12 and 6 Hz); 4.56 (1H, doublet, J=10 Hz); 4.72 (1H, doublet, J=10 Hz); 4.8-5.3 (1H, broad); 5.10 (1H, quintet, J=7 Hz); 7.0-7.7 (1H, broad); 7.33 (5H, singlet); 7.43 (5H, singlet).

(4S)-3-Benzoyl-4-[(S)-α-methylbenzylcarbamoyl]-thiazolidine (Compound No. 117)

Melting Point: 111°-112° C.
$[\alpha]^{23}$ +100.1° (C=1.0, methanol).
Infrared Absorption Spectrum (KBr) $\nu_{max}$cm$^{-1}$: 3350, 1661, 1643.

Nuclear Magnetic Resonance Spectrum (CDCl$_3$) δ ppm: 1.46 (3H, doublet, J=7 Hz); 3.20 (1H, doublet of doublets, J=12 and 7.5 Hz); 3.55 (1H, doublet of doublets, J=12 and 6 Hz); 4.36 (1H, doublet, J=10 Hz); 4.59 (1H, doublet, J=10 Hz); 4.86-5.33 (1H, broad); 5.10 (1H, quintet, J=7 Hz) 7.0-7.7 (1H, broad); 7.26 (5H, singlet); 7.43 (5H, singlet).

(4S)-3-Benzoyl-4-[(R)-α-methylbenzylcarbamoyl]-thiazolidine (Compound No. 118)

Melting Point: 101°-102° C.
$[\alpha]^{23}$ +296.6 (C=1.0, methanol).
Infrared Absorption Spectrum (KBr) $\nu_{max}$cm$^{-1}$: 3350, 3300, 1668, 1630.

Nuclear Magnetic Resonance Spectrum (CDCl$_3$) δ ppm: 1.47 (3H, doublet, J=7 Hz); 3.14 (1H, doublet of doublets, J=12 and 7.5Hz); 3.55 (1H, doublet of doublets, J=12 and 6 Hz); 4.55 (1H, doublet, J=10 Hz); 4.71 (1H, doublet, J=10 Hz); 4.8-5.3 (1H, broad); 5.17 (1H, quintet, J=7 Hz); 7.33 (5H, singlet); 7.43 (5H, singlet).

(4R)-3-Benzoyl-4-[(RS)-α-methylbenzylcarbamoyl]-thiazolidine (Compound No. 119)

Amorphous.
$[\alpha]^{23}$ −196.0° (C=1.0, methanol).
Infrared Absorption Spectrum (KBr) $\nu_{max}$cm$^{-1}$: 3300, 1660, 1640.

Nuclear Magnetic Resonance Spectrum (CDCl$_3$) δ ppm: 1.46 (1.5H, doublet, J=7.5 Hz); 1.47 (1.5H, doublet, J=7.5 Hz) 3.13 (0.5H, doublet of doublets, J=12 and 6 Hz); 3.14 (0.5H, doublet of doublets, J=12 and 6 Hz); 3.53 (0.5H, doublet of doublets, J=12 and 6 Hz); 3.56 (0.5H, doublet of doublets, J=12 and 6 Hz); 4.35 (0.5H, doublet, J=9 Hz); 4.54 (0.5H, doublet, J=9 Hz); 4.61 (0.5H, doublet, J=9 Hz); 4.75 (0.5H, doublet, J=9 Hz); 4.8-5.4 (2H, multiplet); 7.0-7.7 (10H, multiplet).

(4R)-3-Benzoyl-4-[(R)-α-methyl-p-hydroxybenzylcarbamoyl]thiazolidine (Compound No. 120)

Melting at 192°-193° C.
$[\alpha]^{22}$ −73.5° (C=1.0, methanol).
Elemental Analysis: Calculated: C, 64.02%; H, 5.66%; N, 7.86%; S, 9.00%. Found: C, 63.88%; H, 5.76%; N, 7.73%; S, 9.25%.
Infrared Absorption Spectrum (KBr) $\nu_{max}$cm$^{-1}$: 3250, 1675, 1620.

Nuclear Magnetic Resonance Spectrum (CDCl$_3$) δ ppm: 1.33 (3H, doublet, J=7.5 Hz); 3.10 (1H, AB-doublet of doublets, J=12.0 and 4.5 Hz); 3.36 (1H, AB-doublet of doublets, J=12.0 and 9.0 Hz); 4.40-5.10 (2H+1H+1H); 6.71 (2H, doublet, J=9.0 Hz); 7.11 (2H, doublet, J=9.0 Hz); 7.48 (5H, singlet); 8.33 (1H, doublet, J=7.5 Hz); 9.25 (1H, singlet).

(1S,4R)-3-Benzoyl-4-[(R)-α-methyl-p-hydroxybenzylcarbamoyl]-1-oxothiazolidine (Compound No. 121)

Melting at 172°–173° C.
[α]$^{23}$ +19.7° (C=1.0, methanol).
Elemental Analysis: Calculated: C, 61.27%; H, 5.41%; N, 7.52%; S, 8.61%. Found: C, 61.23%; H, 5.31%; N, 7.43%; S, 8.83%.
Infrared Absorption Spectrum (KBr) $\nu_{max}$cm$^{-1}$: 3100, 1680, 1668, 1642.
Nuclear Magnetic Resonance Spectrum [(CD$_3$)$_2$SO] δ ppm: 1.33 (3H, doublet, J=7.5 Hz); 3.10 (1H, AB-doublet of doublets, J=13.5 and 4.5 Hz); 3.63 (1H, AB-doublet of doublets, J=13.5 and 9.0 Hz); 4.32 (1H, AB-doublet, J=12.0 Hz); 4.86 (1H, quartet of doublets, J=7.5 and 7.5 Hz); 4.70–5.10 (1H, broad); 5.26 (1H, AB-doublet, J=12.0 Hz); 6.70 (2H, doublet, J=9.0 Hz); 7.11 (2H, doublet, J=9.0 Hz); 7.51 (5H, singlet); 8.33–8.73 (1H, broad); 9.26 (1H, singlet).

(4R)-3-(p-Hydroxybenzoyl)-4-[(R)-α-methylbenzylcarbamoyl]thiazolidine (Compound No. 122)

Amorphous powder.
[α]$^{23}$ −100.4° (C=1.0, methanol).
Infrared Absorption Spectrum (KBr) $\nu_{max}$cm$^{-1}$: 3700–2400, 3270, 1659.
Nuclear Magnetic Resonance Spectrum (CDCl$_3$) δ ppm: 1.36 (3H, doublet, J=7.5 Hz); 3.45 (1H, AB-doublet of doublets, J=12.0 and 6.0 Hz); 3.75 (1H, AB-doublet of doublets, J=12.0 and 9.0 Hz); 4.63 (1H, AB-doublet, J=13.5 Hz); 4.80 (1H, AB-doublet, J=13.5 Hz); 4.88 (1H, quartet of doublets, J=7.5 and 7.5 Hz); 5.00–5.50 (1H, broad); 6.71 (2H, doublet, J=9.0 Hz); 7.11 (2H, doublet, J=9.0 Hz); 7.50 (5H, singlet); 8.51 (1H, doublet, J=7.5 Hz); 9.20 (1H, singlet).

(4R)-3-(p-Methylbenzoyl)-4-[(R)-α-methylbenzylcarbamoyl]thiazolidine (Compound No. 123)

Melting at 54°–55° C.
[α]$^{23.5}$ −100.3° (C=1.0, methanol).
Elemental Analysis: Calculated: C, 67.77%; H, 6.26%; N, 7.90%; S, 9.05%. Found: C, 67.40%; H, 6.50%; N, 7.78%, S, 9.01%.
Infrared Absorption Spectrum (KBr) $\nu_{max}$cm$^{-1}$: 3280, 1660 (shoulder), 1640.
Nuclear Magnetic Resonance Spectrum (CDCl$_3$) δ ppm: 1.46 (3H, doublet, J=7.5 Hz); 3.15 (1H, AB-doublet of doublets, J=12.0 and 7.5 Hz); 3.61 (1H, AB-doublet of doublets, J=12.0 and 6.0 Hz); 4.36 (1H, AB-doublet, J=9.0 Hz); 4.63 (1H, AB-doublet, J=9.0 Hz); 5.10 (1H, quartet of doublets, J=7.5 and 7.5 Hz); 7.20 (2H, doublet, J=7.5 Hz); 7.29 (5H, singlet); 7.31 (2H, doublet, J=7.5 Hz).

(4R)-3-Benzylsulfonyl-4-[(R)-α-methylbenzylcarbamoyl]-thiazolidine (Compound No. 104)

Melting at 116°–117° C.
[α]$^{23}$ −92.6° (C=1.0, methanol).
Elemental Analysis: Calculated: C, 58.44%; H, 5.68%; N, 7.17%; S, 16.48%. Found: C, 58.33%; H, 5.59%; N, 7.05%; S, 16.66%.
Infrared Absorption Spectrum (KBr) $\nu_{max}$cm$^{-1}$: 3345, 1659.
Nuclear Magnetic Resonance Spectrum (CDCl$_3$) δ ppm: 1.46 (3H, doublet, J=7.5 Hz); 3.10 (1H, AB-doublet of doublets, J=12.0 and 7.5 Hz); 3.48 (1H, AB-doublet of doublets, J=12.0 and 4.5 Hz); 4.16 (1H, AB-doublet, J=9.0 Hz); 4.50 (1H, AB-doublet, J=9.0 Hz); 5.08 (1H, quartet of doublets, J=7.5 and 7.5 Hz); 6.82 (1H, doublet, J=7.5 Hz); 7.31 (5H, singlet); 7.42 (5H, singlet).

(4R)-3-(2-Thenoyl-4-[(R)-α-methylbenzylcarbamoyl]-thiazolidine (Compound No. 124)

Melting at 142°–143° C.
[α]$^{23}$ −70.1 (C=1.0, methanol).
Elemental Analysis: Calculated: C, 58.93%; H, 5.24%; N, 8.08%; S, 18.51%. Found: C, 58.87%; H, 5.25%; N, 8.01%; S, 18.65%.
Infrared Absorption Spectrum (KBr) $\nu_{max}$cm$^{-1}$: 3300, 3260, 1640.
Nuclear Magnetic Resonance Spectrum (CDCl$_3$) δ ppm: 1.47 (3H, doublet, J=7.5 Hz); 3.20 (1H, AB-doublet of doublets, J=12.0 and 7.5 Hz); 3.60 (1H, AB-doublet of doublets, J=12.0 and 4.5 Hz); 4.63 (1H, AB-doublet, J=9.0 Hz); 4.97 (1H, AB-doublet, J=9.0 Hz); 5.21 (1H, quartet of doublets, J=7.5 and 7.5 Hz); 6.80–7.30 (1H, broad); 7.08 (1H, doublet of doublets, J=4.5 and 4.5 Hz); 7.30 (5H, singlet); 7.46 (1H, doublet, J=4.5 Hz); 7.55 (1H, doublet, J=4.5 Hz).

(4R)-3-Nicotinoyl-4-[(R)-α-methylbenzylcarbamoyl]-thiazolidine (Compound No. 125)

Melting at 110°–111° C.
[α]$^{23}$ −108.0° (C=1.0, methanol).
Elemental Analysis: Calculated: C, 63.32%; H, 5.61%; N, 12.31%; S, 9.39%. Found: C, 63.46%; H, 5.53%; N, 12.36%; S, 9.65%.
Infrared Absorption Spectrum (KBr) $\nu_{max}$cm$^{-1}$: 3250, 1690, 1635.
Nuclear Magnetic Resonance Spectrum (CDCl$_3$) δ ppm: 1.49 (3H, doublet, J=7.5 Hz); 3.21 (1H, AB-doublet of doublets, J=12.0 and 7.8 Hz); 3.65 (1H, AB-doublet of doublets, J=12.0 and 6.0 Hz); 4.46 (1H, AB-doublet, J=9.0 Hz); 4.56 (1H, AB-doublet, J=9.0 Hz); 5.10 (1H, quartet of doublets, J=7.5 and 7.5 Hz); 6.80–7.50 (1H, broad); 7.30 (5H, singlet); 7.35 (1H, doublet of doublets, J=7.5 and 4.5 Hz); 7.76 (1H, doublet of doublet of doublets, J=7.5 and 4.5 and 1.5 Hz); 8.65–8.80 (2H, broad).

(4R)-3-Benzoyl-4-benzylcarbamoylthiazolidine (Compound No. 138)

Melting at 119°–120° C.
[α]$^{23.5}$ −177.9° (C=1.0, methanol).
Elemental Analysis: Calculated: C, 66.23%; H, 5.56%; N, 8.58%; X, 9.82%. Found: C, 66.16%; H, 5.45%; N, 8.61%; S, 9.71%.
Infrared Absorption Spectrum (KBr) $\nu_{max}$cm$^{-1}$: 3280, 1690, 1660, 1650.
Nuclear Magnetic Resonance Spectrum (CDCl$_3$) δ ppm: 3.17 (1H, AB-doublet of doublets, J=12.0 and 7.5 Hz); 3.60 (1H, AB-doublet of doublets, J=12.0 and 6.0 Hz); 4.45 (2H, doublet, J=6.0 Hz); 4.46 (1H, AB-doublet, J=9.0 Hz); 4.69 (1H, AB-doublet, J=9.0 Hz); 5.11 (1H, doublet of doublets, J=7.5 and 6.0 Hz); 7.30 (5H, singlet); 7.45 (5H, singlet); 7.00–7.63 (1H, broad).

(4R)-3-Benzoyl-4-(2,4-dichlorobenzylcarbamoyl)-thiazolidine (Compound No. 139)

Melting at 130.5°–132° C.
[α]$^{23.5}$ −133.1° (C=1.0, methanol).

Elemental Analysis: Calculated: C, 54.69%; H, 4.08%; N, 7.08%; S, 8.11%; Cl, 17.93%. Found: C, 54.63%; H, 4.09%; N, 7.18%; S, 8.23%; Cl, 17.70%.

Infrared Absorption Spectrum (KBr) $\nu_{max}$ cm$^{-1}$: 3270, 1682, 1628.

Nuclear Magnetic Resonance Spectrum (CDCl$_3$) δ ppm: 3.20 (1H, AB-doublet of doublets, J=12.0 and 7.5 Hz); 3.62 (1H, AB-doublet of doublets, J=12.0 and 6.0 Hz); 4.50 (1H, AB-doublet, J=9.0 Hz); 4.51 (2H, doublet, J=6.0 Hz); 4.68 (1H, AB-doublet, J=9.0 Hz); 5.14 (1H, doublet of doublets, J=7.5 and 6.0 Hz); 7.00–7.65 (1H+3H, multiplet); 7.49 (5H, singlet).

(4R)-3-Benzoyl-4-(α,α-dimethyl-p-chlorobenzylcarbamoyl)thiazolidine (Compound No. 126)

Amorphous powder.

$[α]^{23.5}$ −177.4° (C=1.0, methanol).

Elemental Analysis: Calculated: C, 61.77%; H, 5.44%; N, 7.20%; S, 8.24%; Cl, 9.11%. Found: C, 61.38%; H, 5.24%; N, 6.98%; S, 8.40%; cl, 8.79%.

Infrared Absorption Spectrum (KBr) $\nu_{max}$ cm$^{-1}$: 3300, 1668, 1630. Nuclear Magnetic Resonance Spectrum (CDCl$_3$) δ ppm: 1.63 (3H, singlet); 1.72 (3H, singlet); 3.17 (1H, AB-doublet of doublets, J=12.0 and 7.5 Hz); 3.63 (1H, AB-doublet of doublets, J=12.0 and 6.0 Hz); 4.47 (1H, AB-doublet, J=9.0 Hz); 4.63 (1H, AB-doublet, J=9.0 Hz); 5.06 (1H, doublet of doublets, J=7.5 and 6.0 Hz); 6.84–7.78 (1H, broad); 7.30 (5H, singlet); 7.52 (4H, singlet).

EXAMPLE 25

(1R,4R)-3-Benzoyl-4-[(R)-α-methylbenzylcarbamoyl]-1-oxothiazolidine (Compound No. 127)

To a solution of 507 mg of (1R,4R)-3-benzoyl-1-oxothiazolidine-4-carboxylic acid (prepared as described in Preparation 10) in 6 ml of N,N-dimethylformamide were added 242 mg of (R)-α-methylbenzylamine, 306 mg of N-hydroxybenzotriazole hydrate and 413 mg of dicyclohexylcarbodiimide, and the mixture was stirred at room temperature for 3 hours. At the end of this time, 25 ml of ethyl acetate were added to the reaction mixture and the insolubles were filtered off. The filtrate was washed, in turn, with 10 ml of water, 15 ml of 0.1N hydrochloric acid, 15 ml of water, 15 ml of a 4% w/v aqueous solution of sodium bicarbonate and 15 ml of water and then dried over anhydrous sodium sulfate. The solvent was distilled off and ethyl acetate was added to the residue to assist the filtration of the insolubles.

The filtrate was concentrated by evaporation under reduced pressure to leave crystals, which were recrystallized from a 1:1 by volume mixture of ethyl acetate and diethyl ether to give 680 mg of the title compound melting at 138°–139° C.

$[α]^{24}$ −157° (C=1.0, methanol).

Infrared Absorption Spectrum (KBr) $\nu_{max}$ cm$^{-1}$: 3300, 3070, 2990, 2940, 1675, 1650, 1600.

Mass spectrum (m/e): 356 (M$^+$).

Nuclear Magnetic Resonance Spectrum (CDCl$_3$) δ ppm: 1.46 (3H, doublet, J=7.5 Hz); 3.23 (1H, doublet of doublet of doublets, J=2 and 8 and 14 Hz); 3.57 (1H, doublet of doublets, J=8 and 14 Hz); 3.97 (1H, doublet, J=12 Hz); 4.77 (1H, broad doublet, J=12 Hz); 5.03 (1H, multiplet); 5.67 (1H, triplet, J=8 Hz); 7.27 (5H, singlet); 7.46 (5H, singlet); 7.70 (1H, doublet, J=9 Hz).

EXAMPLE 26

(1S,4R)-3-Benzoyl-4-](R)-α-methylbenzylcarbamoyl]-1-oxothiazolidine (Compound No. 128)

To a solution of 760 mg of (1S,4R)-3-benzoyl-1-oxothiazolidine-4-carboxylic acid (prepared as described in Preparation 10) in 10 ml of N,N-dimethylformamide were added 364 mg of (R)-α-methylbenzylamine, 459 mg of N-hydroxybenzotriazole hydrate and 619 mg of dicyclohexylcarbodiimide, and the mixture was stirred at room temperature for 3 hours. The reaction mixture was treated in the same manner as described in Example 25 except that the residue was subjected to column chromatography through 80 g of silica gel, eluted with a 3.5:96.5 by volume mixture of ethanol and methylene chloride, to give an oil. The oil was crystallized by the addition of a 1:1 by volume mixture of isopropanol and cyclohexane to give 820 mg of the title compound melting at 80°–83° C.

$[α]^{24}$ +9.8° (C=1.0, methanol).

Infrared Absorption Spectrum (KBr) $\nu_{max}$ cm$^{-1}$: 3580, 3430, 3300, 3070, 2930, 1685, 1655, 1635, 1600.

Mass spectrum (m/e): 357 (M+1).

Nuclear Magnetic Resonance Spectrum (CDCl$_3$) δ ppm: 1.44 (3H, doublet, J=7 Hz); 3.34 (1H, doublet of doublets, J=14 and 15 Hz); 3.43 (1H, singlet); 4.46 (1H, doublet, J=12 Hz); 4.87 (1H, doublet, J=12 Hz); 5.03 (1H, multiplet); 5.07 (1H, multiplet); 7.29 (5H, singlet); 7.48 (5H, singlet).

EXAMPLE 27

(4R)-3-Benzoyl-4-[(R)-α-methylbenzylcarbamoyl]-1,1-dioxothiazolidine (Compound No. 129)

(a) To a solution of 1.2 g of methoxymethyl (1RS,4R)-3-benzoyl-1-oxothiazolidine-4-carboxylate (obtained by the method described in Preparation 10) in 30 ml of methylene chloride was added 0.82 g of 85% m-chloroperbenzoic acid, and the mixture was stirred at room temperature for 20 hours. The reaction mixture was then washed, in turn, with 30 ml of a 4% w/v aqueous solution of sodium bicarbonate and with 30 ml of water and then concentrated by evaporation under reduced pressure. The residue was subjected to column chromatography through 50 g of silica gel, eluted with a 2.5:97.5 by volume mixture of ethanol and methylene chloride, to give 1.03 g of methoxymethyl (4R)-3-benzoyl-1,1-dioxothiazolidine-4-carboxylate.

(b) The 1.03 g of dioxide obtained as described in step (a) above was dissolved in a mixture of 2.5 ml of trifluoroacetic acid, 5 ml of methanol and 2.5 ml of water, and the solution was stirred at 40° C. for 4 hours. The solvent was then distilled off under reduced pressure to give 0.6 g of (4R)-3-benzoyl-1,1-dioxothiazolidine-4-carboxylic acid in the form of a white powder.

(c) The 0.6 g of carboxylic acid obtained as described in step (b) above was dissolved in 7 ml of N,N-dimethylformamide, and then 0.27 g of (R)-α-methylbenzylamine, 0.30 g of N-hydroxybenzotriazole hydrate and 0.46 g of dicyclohexylcarbodiimide were added, and the mixture was stirred at room temperature for 3 hours. 25 ml of ethyl acetate were added to the reaction mixture and the insolubles were filtered off. The filtrate was washed, in turn, with 10 ml of water, 15 ml of 0.1N hydrochloric acid, 15 ml of water, 15 ml of a 4% aqueous solution of sodium bicarbonate and 15 ml of water and then dried over anhydrous sodium sulfate. The solvent was distilled off and the residue was subjected to column chromatography through 160 g of silica gel, eluted with a 97.5:2.5 by volume mixture of methylene chloride and ethanol, to give an oil, which was crystallized by the addition of benzene to give 0.4 g of the title compound in the form of colorless crystals melting at 132°-133° C.

$[\alpha]^{24}$ +34.2° (C=1.0, methanol).

Infrared Absorption Spectrum (Nujol mull) $\nu_{max}$cm$^{-1}$: 1660, 1645.

Nuclear Magnetic Resonance Spectrum (CDCl$_3$) δ ppm: 1.47 (3H, doublet, J=7.5 Hz); 3.30 (1H, doublet of doublet of doublets, J=1.5 and 9 and 14.5 Hz); 3.98 (1H, doublet of doublets, J=6 and 14.5 Hz); 4.17 (1H, doublet, J=12 Hz); 4.53 (1H, doublet of doublets, J=1.5 and 12 Hz); 5.07 (1H, quintet, J=7.5 Hz); 5.59 (1H, doublet of doublets, J=6 and 9 Hz); 7.27 (5H, singlet); 7.3–7.7 (5H, multiplet).

Examples 28 and 29 described alternative methods of preparing the same compounds whose preparation is described in Examples 25, 26 and 27.

EXAMPLE 28

(1R,4R)-3-Benzoyl-4-[(R)-α-methylbenzylcarbamoyl]-1-oxothiazolidine (Compound No. 127) and (1S,4R)-3-benzoyl-4-[(R)-α-methylbenzylcarbamoyl]-1-oxothiazolidine (Compound No. 128)

To a solution of 5.10 g of (4R)-3-benzoyl-4-[(R)-α-methylbenzylcarbamoyl]thiazolidine (prepared as described in Example 10) in 100 ml of methylene chloride were added, whilst cooling at −5° C., 3.5 g of 85% m-chloroperbenzoic acid, and the mixture was stirred at the same temperature for 30 minutes. The reaction mixture was then washed, in turn, twice with 100 ml of a 4% w/v aqueous solution of sodium bicarbonate and then with 100 ml of water, after which it was dried over anhydrous sodium sulfate. The solvent was distilled off under reduced pressure to leave an oil, which was subjected to column chromatography through 450 g of silica gel. Elution with a 3.5:96.5 by volume mixture of ethanol and methylene chloride gave first 0.241 g of the starting material.

From the second fraction, there were obtained 4.350 g of the title compound having the 1 R configuration. This was crystallized by the addition of a mixture of ethyl acetate and diethyl ether to give colorless crystals melting at 138°-139° C., whose physical properties were identical with those of the compound obtained as described in Example 25.

From the third fraction, there was obtained 0.540 g of the title compound having the 1S configuration in the form of an oil, which was crystallized by the addition of a mixture of isopropanol and cyclohexane to give colorless crystals melting at 80°-83° C. The physical properties of the crystals obtained in this Example were identical with those of the compound obtained as described in Example 26.

EXAMPLE 29

(4R)-3-Benzoyl-4-[(R)-α-methylbenzylcarbamoyl]-1,1-dioxothiazolidine (Compound No. 129)

To a solution of 357 mg of (1R,4R)-3-benzoyl-4-[(R)-α-methylbenzylcarbamoyl]-1-oxothiazolidine (prepared as described in Example 25 or 28 ) in 10 ml of methylene chloride were added 203 mg of 85% m-chloroperbenzoic acid, and the mixture was stirred at room temperature for 20 hours. The reaction mixture was then washed, in turn, with 30 ml of a 4% aqueous solution of sodium bicarbonate and with 30 ml of water and dried over anhydrous sodium sulfate. The solvent was distilled off under reduced pressure to leave an oil, which was then subjected to column chromatography through 80 g of silica gel, eluted with a 97.5:2.5 by volume mixture of methylene chloride and ethanol, to give an oil. This oil was crystallized by the addition of benzene to give 266 mg of the title compound in the form of crystals. The physical properties of these crystals were identical with those of the compound obtained as described in Example 27.

EXAMPLE 30

(1R,4R)-3-Benzoyl-4-[(R)-α-methyl-p-hydroxybenzylcarbamoyl]-1-oxothiazolidine (Compound No. 130)

9.47 g (69.11 mmole) of (R)-α-methyl-p-hydroxybenzylamine (prepared as described in Preparation 13), 10.58 g (69.11 mmole) of N-hydroxybenzotriazole monohydrate and 14.26 g (69.11 mmole) of dicyclohexylcarbodiimide were added in that order to a solution of 17.50 g (69.11 mmole) of (1R,4R)-3-benzoyl-1-oxothiazolidine-4-carboxylic acid (prepared as described in Preparation 10) in 100 ml of dimethylformamide cooled at 5° C., and the mixture was stirred at a temperature between 3° and 6° C. for 30 minutes and then at room temperature for a further 4 hours. At the end of this time, the reaction mixture was filtered and the insolubles were washed with 100 ml of hot dimethylformamide. The filtrate and the washings were combined and concentrated by evaporation under reduced pressure to leave crystals. These crystals were recrystallized from methanol to give 19.21 g (74.6%) of the title compound in the form of colorless needles melting at 233°-234° C.

$[\alpha]^{23}$ −124.5° (C=1.0, methanol),

Elemental analysis: Calculated: C, 61.27%; H, 5.41%; N, 7.52%; S, 8.61%. Found: C, 61.31%; H, 5.34%; N, 7.52%; S, 8.75%.

Infrared Absorption Spectrum (KBr) $\nu_{max}$cm$^{-1}$: 3260, 1659 (shoulder), 1650, 1645.

Nuclear Magnetic Resonance Spectrum [(CD$_3$)$_2$SO] δ ppm: 1.33 (3H, doublet, J=7.5 Hz); 3.08 (1H, AB-doublet of doublets, J=13.5 and 9.0 Hz); 3.46 (1H, AB-doublet of doublets, J=13.5 and 7.5 Hz); 4.30–5.10 (2H+1H); 5.10–5.60 (1H, broad); 6.71 (2H, doublet, J=9.0 Hz); 7.15 (2H, doublet, J=9.0 Hz); 7.51 (5H, singlet); 8.33–8.73 (1H, broad); 9.26 (1H, singlet).

EXAMPLE 31

(4R)-3-Benzoyl-4-[(R)-α-methyl-p-hydroxybenzylcarbamoyl]-1,1-dioxothiazolidine (Compound No. 131)

1.00 g (7.29 mmole) of (R)-α-methyl-p-hydroxybenzylamine (prepared as described in Preparation 13), 1.12 g (7.29 mmole) of N-hydroxybenzotriazole monohydrate and 1.51 g (7.29 mmole) of dicyclohexylcarbodiimide were added in that order to a solution of 1.96 g (7.29 mmole) of (4R)-3-benzoyl-1,1-dioxothiazolidine-4-carboxylic acid (prepared as described in Preparation 12) in 100 ml of dimethylformamide cooled at 5° C., and then the mixture was stirred at a temperature between 3° and 6° C. for 30 minutes and then at room temperature for a further 23 hours. The reaction mixture was filtered, the insolubles were washed with 20 ml of ethyl acetate, and the filtrate and the washings were combined. 50 ml of ethyl acetate were added to the combined mixture, which was washed twice, each time with 50 ml of a 4% w/v aqueous solution of sodium bicarbonate, and the organic phase was separated and dried over anhydrous magnesium sulfate. The solvent was distilled off under reduced pressure and the residue was purified by Lobar column chromatography through silica gel (Merck, Art-10402), eluted with a 2:1 by volume mixture of ethyl acetate and cyclohexane. The eluate was concentrated by evaporation under reduced pressure and the residue was lyophilized with a mixture of acetone and benzene to give 2.04 g (72.0%) of the title compound in the form of a colorless powder.

$[\alpha]^{23}$ −8.7° (C=1.0, methanol),

Infrared Absorption Spectrum (KBr) $\nu_{max}$cm$^{-1}$: 3350, 1660.

Nuclear Magnetic Resonance Spectrum (CDCl$_3$) δ ppm: 1.36 (3H, doublet, J=7.5 Hz); 3.45 (1H, AB-doublet of doublets, J=13.5 and 6.0 Hz); 3.75 (1H, AB-doublet of doublets, J=13.5 and 9.0 Hz); 4.63 (1H, AB-doublet, J=13.5 Hz); 4.80 (1H, AB-doublet, J=13.5 Hz); 4.88 (1H, quartet of doublets, J=7.5 and 7.5 Hz); 5.00–5.50 (1H, broad); 6.71 (2H, doublet, J=9.0 Hz); 7.11 (2H, doublet, J=9.0 Hz); 7.50 (5H, singlet); 8.51 (1H, doublet, J=7.5 Hz); 9.20 (1H, singlet).

EXAMPLE 32

(4R)-3-(4-Fluorobenzoyl)-4-[(R)-α-methylbenzylcarbamoyl)thiazolidine (Compound No. 132)

1.58 g (10 mmole) of p-fluorobenzoyl chloride and 0.79 g (10 mmole) of pyridine were added dropwise to a solution of 2.36 g (10 mmole) of (4R)-[(R)-α-methylbenzylcarbamoyl]thiazolidine (prepared as described in Preparation 14) in 30 ml of dry methylene chloride cooled at 5° C., and then the mixture was stirred at a temperature between 3° and 5° C. for 30 minutes.

The reaction mixture was then washed twice, each time with 30 ml of a 10% w/v aqueous solution of sodium chloride, and the aqueous washings were extracted with 30 ml of methylene chloride. The methylene chloride extract was combined with the washed reaction mixture and dried over anhydrous magnesium sulfate. The solvent was then distilled off under reduced pressure to leave crystals. These crystals were recrystallized from ethyl acetate to give 3.16 g (88.2%) of the title compound in the form of colorless needles melting at 121°–122° C.

$[\alpha]^{23}$ −92.6° (C=1.0, methanol).

Infrared Absorption Spectrum (KBr) $\nu_{max}$cm$^{-1}$: 3470, 3360, 3240, 1665, 1640, 1622.

Nuclear Magnetic Resonance Spectrum (CDCl$_3$) δ ppm: 1.50 (3H, doublet, J=7.5 Hz); 3.40 (1H, AB-doublet of doublets, J=12.0 and 7.8 Hz); 3.66 (1H, AB-doublet of doublets, J=12.0 and 6.0 Hz); 4.40 (1H, AB-doublet, J=9.0 Hz); 4.60 (1H, AB-doublet, J=9.0 Hz); 5.10 (1H, quartet of doublets, J=7.5 and 7.5 Hz); 6.90–7.63 (1H, broad); 6.90–7.63 (4H, multiplet); 7.30 (b 5H, singlet).

We claim:

1. A compound of formula (I):

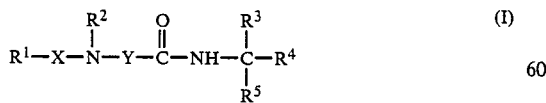

wherein:

R$^1$ is a benzyl group, a phenyl group, a phenyl group having 1 or 2 substituents selected from the group consisting of C$_1$–C$_4$ alkyl, halogen, C$_1$–C$_4$ alkoxy, hydroxy, carboxy, nitro, trifluoromethyl, amino, C$_1$–C$_4$ alkylamino, dialkylamino wherein each alkyl part is C$_1$–C$_4$ alkyl, C$_1$–C$_4$ acylamino, C$_1$–C$_4$ alkanoyl, cyano, carbamoyl, alkylcarbamoyl wherein the alkyl part is C$_1$–C$_4$ alkyl, dialkylcarbamoyl wherein each alkyl part is C$_1$–C$_4$ alkyl and C$_1$–C$_4$ alkylthio substituents, a naphthyl group, a thienyl group or a pyridyl group;

X is a carbonyl or sulfonyl group;

R$^3$ is hydrogen or methyl;

R$^4$ is hydrogen or methyl;

Y and R$^2$ together with the nitrogen to which they are attached, form a group of the formula

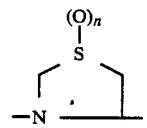

wherein n is 0, 1 or 2; and

R$^5$ is a C$_1$–C$_4$ alkyl group, a phenyl group, a phenyl group having 1 or 2 substituents selected from the group consisting of C$_1$–C$_4$ alkyl, halogen, C$_1$–C$_4$ alkoxy, hydroxy, carboxy, nitro, trifluoromethyl, amino, C$_1$–C$_4$ alkylamino, dialkylamino wherein each alkyl part is C$_1$–C$_4$ alkyl, C$_1$–C$_4$ acylamino, C$_1$–C$_4$ alkanoyl, cyano, carbamoyl, alkylcarbamoyl wherein the alkyl part is C$_1$–C$_4$ alkyl, dialkylcarbamoyl wherein each alkyl part is C$_1$–C$_4$ alkyl and C$_1$–C$_4$ alkylthio substituents.

2. A compound as claimed in claim 1, wherein:

R$^1$ represents a benzyl group, a phenyl group, a phenyl group having one or two substituents selected from the group consisting of C$_1$–C$_3$ alkyl, halogen, C$_1$–C$_4$ alkoxy, hydroxy, carboxy, nitro, amino, C$_1$–C$_4$ alkylamino, dialkylamino wherein each alkyl part is C$_1$–C$_4$, C$_1$–C$_4$ aliphatic carboxylic acylamino, cyano and C$_1$–C$_4$ alkylthio substituents, a naphthyl group, a thienyl group or a pyridyl group;

X represents a carbonyl or sulfonyl group; and R$^5$ represents a C$_1$–C$_4$ alkyl group, a phenyl group or a phenyl group having 1 or 2 substituents selected from the group consisting of C$_1$–C$_3$ alkyl, halogen and hydroxy substituents.

3. A compound as claimed in claim 1, wherein:

R$^1$ represents a benzyl group, a phenyl group, a phenyl group having one or two substituents selected from the group consisting of C$_1$–C$_3$ alkyl, halogen, C$_1$–C$_4$ alkoxy, hydroxy, carboxy, nitro, amino, C$_1$–C$_4$ alkylamino, dialkylamino wherein each alkyl part is C$_1$–C$_4$, C$_1$–C$_4$ aliphatic carboxylic acylamino, trifluoromethyl, C$_1$–C$_4$ alkanoyl, carbamoyl, alkylcarbamoyl wherein the alkyl part is C$_1$–C$_4$ alkyl, cyano, and C$_1$–C$_4$ alkylthio substituents, a naphthyl group, a thienyl group or a pyridyl group;

X represents a carbonyl or sulfonyl group;

R$^5$ represents a C$_1$–C$_4$ alkyl group, a phenyl group or a phenyl group having 1 or 2 substituents selected from the group consisting of C$_1$–C$_4$ alkyl, halogen, C$_1$–C$_4$ alkoxy, carboxy, nitro, trifluoromethyl, amino, C$_1$–C$_4$ alkylamino, dialkylamino wherein each alkyl part is C$_1$–C$_4$ alkyl, C$_1$–C$_4$ acylamino, C$_1$–C$_4$ alkanoyl, cyano, carbamoyl, alkylcarbamoyl wherein the alkyl part is C$_1$–C$_4$ alkyl, dialkylcarbamoyl wherein each alkyl part is C$_1$–C$_4$ alkyl, C$_1$–C$_4$ alkylthio and hydroxy substituents.

4. A compound as claimed in claim 1, wherein;
R$^1$ represents a benzyl group, a phenyl group or a phenyl group having a 1 or 2 halogen substituents;
R$^5$ represents a C$_1$–C$_4$ alkyl group or a phenyl group.

5. A compound as claimed in claim 1, wherein:
R$^1$ represents a phenyl group;
X represents a carbonyl group;
R$^5$ represents the phenyl group.

6. The compound of claim 1, designated (4R)-3-Benzoyl-4-[(R)-α-methylbenzylcarbamoyl]thiazolidine.

7. The compound of claim 1, designated (4R)-3-Benzoyl-4-[(S)-α-methylbenzylcarbamoyl]thiazolidine.

8. The compound of claim 1, designated (4S)-3-Benzoyl-4-[(S)-α-methylbenzylcarbamoyl]thiazolidine.

9. The compound of claim 1, designated (4S)-3-Benzoyl-4-[(R)-α-methylbenzylcarbamoyl]thiazolidine.

10. The compound of claim 1, designated (4R)-3-Benzoyl-4-[(RS)-α-methylbenzylcarbamoyl]thiazolidine.

11. The compound of claim 1, designated (1R,4R)-3-Benzoyl-4-[(R)-α-methylbenzylcarbamoyl]-1-oxothiazolidine.

12. The compound of claim 1, designated (1S,4R)-3-Benzoyl-4-[(R)-α-methylbenzylcarbamoyl]-1-oxothiazolidine.

13. The compound of claim 1, designated (4R)-3-Benzoyl-4-[(R)-α-methylbenzylcarbamoyl]-1,1-dioxothiazolidine.

14. The compound of claim 1, designated (4R)-3-Benzoyl-4-benzylcarbamoylthiazolidine.

15. A method of treating a transplanted tumor in a mammal comprising administering an effective amount of the compound of claim 1.

* * * * *

UNITED STATES PATENT AND TRADEMARK OFFICE
CERTIFICATE OF CORRECTION

PATENT NO. : 4,904,680

DATED : February 27, 1990

INVENTOR(S) : MATSUI et al

It is certified that error appears in the above-identified patent and that said Letters Patent is hereby corrected as shown below:

On the title page:

Insert under "U.S. PATENT DOCUMENTS":

3,647,775  3/1972  Marquarding et al
    3,657,341  4/1972  Thorne
    4,579,581  4/1986  Kay et al Insert under "OTHER DOCUMENTS":

Dobashi et al, JACS 107(12), 3406-11 (1985)
    Pirkle et al, J. Ag. Chem. 49(17), 3043-6 (1984)
    Gieren et al, Tetrahedron Letters, 18, 1503-6 (1977)
    Makovec et al, Arzneim-Forsch, 35(11) No.7, 1048-51 (1985)
    Prikle et al, J. Org. Chem., 44(12), 1957-60 (1979)
    Antonjuk et al, J. Chem. Soc. Perkin Trans. I, 1989-2003 (1984)
    Ginsburg et al, JACS, 86(21), 4716-20 (1964)
    Knobler et al, J. Org. Chem. 29(5), 1229-36 (1964)

Sheradsky et al  CA 55:24580H
    Shemuakin et al  CA 54:7632e
    Neth 6,510,006  CA 65:3793a
    Rovati et al    CA 68:58463y
    Schwyzer et al  CA 53:21699h Under "FOREIGN PATENT DOCUMENTS", right column, second reference, change the country "Fed. Rep. of Germany" to --Austria--.

UNITED STATES PATENT AND TRADEMARK OFFICE
CERTIFICATE OF CORRECTION

PATENT NO. : 4,904,680

DATED : February 27, 1990

INVENTOR(S) : MATSUI et al

It is certified that error appears in the above-identified patent and that said Letters Patent is hereby corrected as shown below:

Column 44, line 58 (claim 3), insert --and-- following "group;".

Column 45, line 3 (claim 4), insert --and-- following "substituents;".

Column 45, line 7 (claim 5), insert --and-- following "group;".

Signed and Sealed this

Seventh Day of July, 1992

Attest:

DOUGLAS B. COMER

Attesting Officer

Acting Commissioner of Patents and Trademarks